(12) United States Patent
Suzuki et al.

(10) Patent No.: US 10,561,298 B2
(45) Date of Patent: Feb. 18, 2020

(54) POSITION DETECTION SYSTEM AND POSITION DETECTION METHOD

(71) Applicant: OLYMPUS CORPORATION, Tokyo (JP)

(72) Inventors: Yusuke Suzuki, Hino (JP); Atsushi Chiba, Hachioji (JP); Hironao Kawano, Machida (JP); Atsushi Kimura, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 412 days.

(21) Appl. No.: 15/648,619

(22) Filed: Jul. 13, 2017

(65) Prior Publication Data

US 2017/0311773 A1 Nov. 2, 2017

Related U.S. Application Data

(63) Continuation of application No. PCT/JP2015/081382, filed on Nov. 6, 2015.

(30) Foreign Application Priority Data

Mar. 16, 2015 (JP) .................. 2015-052610
Mar. 16, 2015 (JP) .................. 2015-052654

(51) Int. Cl.
*A61B 1/00* (2006.01)
*A61B 5/06* (2006.01)
*A61B 1/04* (2006.01)

(52) U.S. Cl.
CPC ...... *A61B 1/00009* (2013.01); *A61B 1/00016* (2013.01); *A61B 1/00158* (2013.01);
(Continued)

(58) Field of Classification Search
CPC ..... A61B 5/073; A61B 5/062; A61B 1/00009; A61B 1/00158; A61B 1/00016; A61B 1/00025; A61B 1/041; A61B 2562/046
See application file for complete search history.

(56) References Cited

U.S. PATENT DOCUMENTS 8,260,398 B2 9/2012 Uchiyama et al.
2010/0204566 A1 8/2010 Uchiyama et al.
(Continued)

FOREIGN PATENT DOCUMENTS

JP 2008-132047 A 6/2008
JP 2009-039356 A 2/2009
(Continued)

OTHER PUBLICATIONS

International Search Report dated Feb. 9, 2016 issued in PCT/JP2015/081382.

*Primary Examiner* — Bo Joseph Peng
(74) *Attorney, Agent, or Firm* — Scully, Scott, Murphy & Presser, P.C.

(57) ABSTRACT

A position detection system includes: a capsule medical device configured to generate a position-detecting magnetic field; a plurality of detection coils arranged outside a subject; and a processor including hardware. The processor is configured to correct a magnetic field component caused by a first magnetic field generation material with respect to each of measurement values of detection signals output from the detection coils, the first magnetic field generation material being arranged inside a space that the position-detecting magnetic field generated by the capsule medical device present inside a detection target region is reachable, the detection target region being a region in which a position of the capsule medical device is detectable, the first magnetic field generation material being configured to generate a
(Continued)

magnetic field due to action of the position-detecting magnetic field.

15 Claims, 13 Drawing Sheets

(52) U.S. Cl.
CPC .......... *A61B 5/062* (2013.01); *A61B 1/00025* (2013.01); *A61B 1/041* (2013.01)

(56) References Cited

U.S. PATENT DOCUMENTS

| | | |
|---|---|---|
| 2010/0305426 A1 | 12/2010 | Kimura et al. |
| 2011/0181273 A1 | 7/2011 | Iida et al. |
| 2011/0184690 A1 | 7/2011 | Iida et al. |
| 2014/0187918 A1* | 7/2014 | Higaki .................. A61B 1/041 |
| | | 600/424 |

FOREIGN PATENT DOCUMENTS

| | | |
|---|---|---|
| WO | WO 2010/061893 A1 | 6/2010 |
| WO | WO 2010/103866 A1 | 9/2010 |
| WO | WO 2010/106856 A1 | 9/2010 |

* cited by examiner

FIG.14
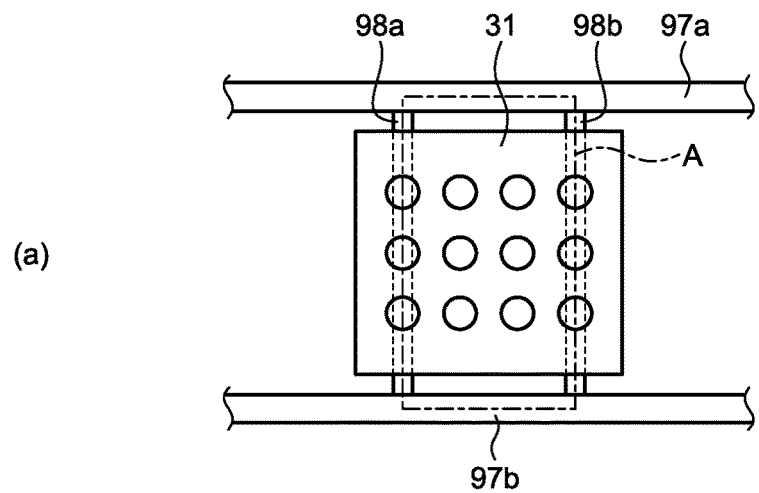
(a)
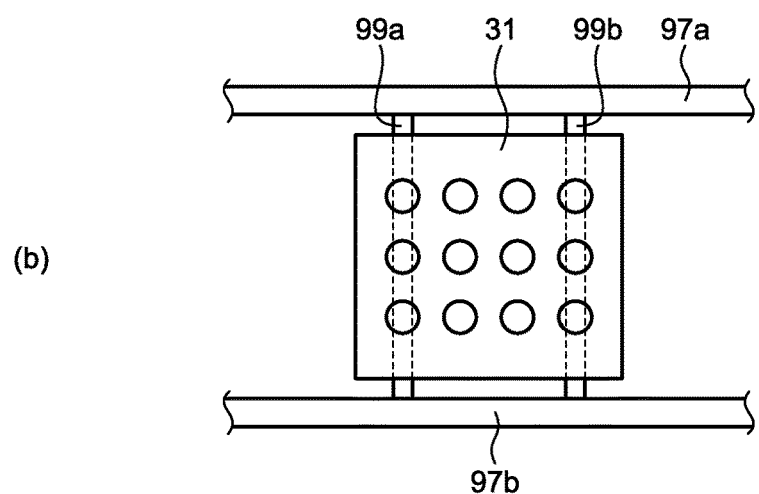
(b)
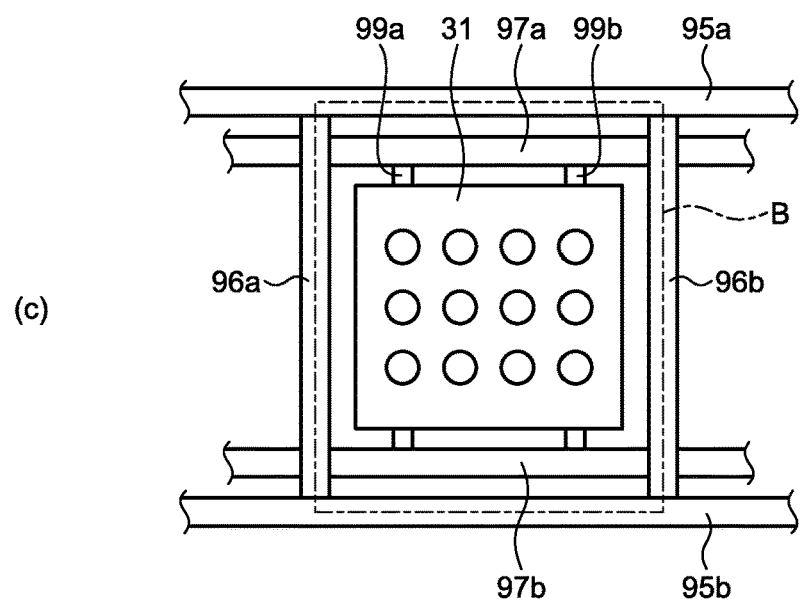
(c)

POSITION DETECTION SYSTEM AND POSITION DETECTION METHOD

CROSS REFERENCES TO RELATED APPLICATIONS

This application is a continuation of PCT international application Ser. No. PCT/JP2015/081382 filed on Nov. 6, 2015 which designates the United States, incorporated herein by reference, and which claims the benefit of priority from Japanese Patent Applications No. 2015-052610, filed on Mar. 16, 2015 and Japanese Patent Applications No. 2015-052654, filed on Mar. 16, 2015, incorporated herein by reference.

BACKGROUND

1. Technical Field

The disclosure relates to a position detection system and a position detection method which detects a position and a posture of a capsule medical device introduced into a subject.

2. Related Art

Recently, a capsule medical device, which is introduced into a subject and acquires various types of information relating to the subject or administers a medicine to the subject, has been developed. For example, a capsule endoscope, which is formed in a size that can be introduced into a digestive tract of the subject, has been known. The capsule endoscope has an imaging function and a wireless communication function inside a casing formed in a capsule shape, performs imaging while moving inside the digestive tract after being swallowed by the subject, and sequentially performs wireless transmission of image data of an image inside an organ of the subject. Hereinafter, the image inside the subject will be referred to also as an in-vivo image.

In addition, a system, which detects a position of such a capsule medical device inside a subject, has been also developed. For example, JP 2008-132047 A discloses a position detection system that includes a capsule medical device with a built-in magnetic field generation coil, which generates a magnetic field by supplying power and a magnetic field detection coil which detects the magnetic field generated by the magnetic field generation coil outside a subject, and performs an operation of detecting a position of the capsule medical device based on the intensity of the magnetic field detected by the magnetic field detection coil. Hereinafter, the magnetic field detection coil will be simply referred to also as a detection coil.

SUMMARY

In some embodiments, a position detection system includes: a capsule medical device configured to generate a position-detecting magnetic field and configured to be introduced into a subject; a plurality of detection coils arranged outside the subject, each detection coil being configured to detect the position-detecting magnetic field to output detection signal; and a processor including hardware. The processor is configured to correct a magnetic field component caused by a first magnetic field generation material with respect to each of measurement values of detection signals output from the detection coils, the first magnetic field generation material being arranged inside a space that the position-detecting magnetic field generated by the capsule medical device present inside a detection target region is reachable, the detection target region being a region in which a position of the capsule medical device is detectable, the first magnetic field generation material being configured to generate a magnetic field due to action of the position-detecting magnetic field. The processor is configured to correct the magnetic field component using a first correction factor which is a function of a measurement value of the position-detecting magnetic field detected by the detection coil in a state where the first magnetic field generation material is arranged inside the space and the capsule medical device is arranged at a specific position inside the detection target region, and a measurement value of the position-detecting magnetic field detected by the detection coil in a state where the first magnetic field generation material is not arranged inside the space and the capsule medical device is arranged at the specific position.

In some embodiments, a position detection method includes: detecting a position-detecting magnetic field to output a detection signal using each of a plurality of detection coils arranged outside a subject, the position-detecting magnetic field being generated by a capsule medical device introduced into the subject; and correcting a magnetic field component caused by a magnetic field generation material with respect to each of measurement values of detection signals output from the detection coils, the magnetic field generation material being arranged inside a space that the position-detecting magnetic field generated by the capsule medical device present inside a detection target region is reachable, the detection target region being a region in which a position of the capsule medical device is detectable, the magnetic field generation material being configured to generate a magnetic field due to action of the position-detecting magnetic field. The correcting includes correcting the magnetic field component using a correction factor which is a function of a measurement value of the position-detecting magnetic field detected by the detection coil in a state where the magnetic field generation material is arranged inside the space and the capsule medical device is arranged at a specific position inside the detection target region, and a measurement value of the position-detecting magnetic field detected by the detection coil in a state where the magnetic field generation material is not arranged inside the space and the capsule medical device is arranged at the specific position.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 14 is a schematic view for describing a method of acquiring a correction factor in a case where the support frame illustrated in FIG. 13 is configured as an interference magnetic field generation source.

DETAILED DESCRIPTION

Hereinafter, a position detection system and a position detection method according to embodiments of the disclosure will be described with reference to the drawings. Incidentally, a capsule endoscope, which is orally introduced into a subject and captures the inside of a digestive tract of the subject, is exemplified as a mode of a capsule medical device serving as a detection target of a position detection system in the embodiments to be described hereinafter. However, the disclosure is not limited to these embodiments. That is, the disclosure can be applied to position detection of various medical devices formed in a capsule type, for example, a capsule endoscope which moves inside the lumen from the esophagus to the anus of the subject, a capsule medical device which delivers a medicine or the like into the subject, a capsule medical device which includes a PH sensor that measures a PH inside the subject, and the like.

In addition, the respective drawings referred to in the following description schematically illustrate shapes, sizes, and positional relationships merely to such a degree that the content of the disclosure is understandable. Accordingly, the disclosure is not limited only to the shapes, sizes, and positional relationships exemplified in the respective drawings. Incidentally, the same parts are denoted by the same reference signs in the description of the drawings.

First Embodiment

Figure 1:
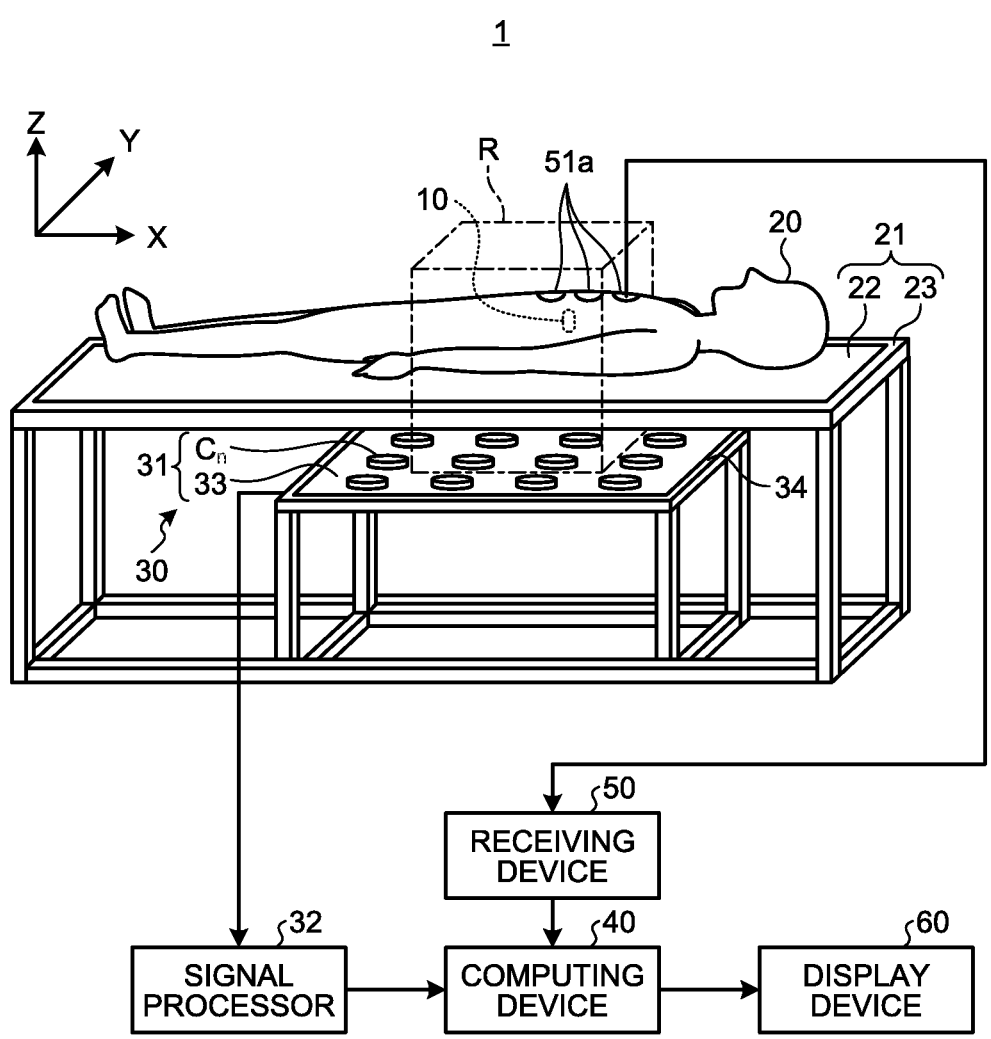
FIG. 1 is a schematic view illustrating the overview of a position detection system according to a first embodiment of the disclosure.

FIG. 1 is a schematic view illustrating the overview of a position detection system according to a first embodiment of the disclosure. As illustrated in FIG. 1, a position detection system 1 according to the first embodiment is a system that detects a position of a capsule endoscope, which is an example of a capsule medical device and is introduced into a subject 20 to capture the inside of the subject 20, and includes a capsule endoscope 10, a bed 21 on which the subject 20 is placed, a magnetic field detection device 30 which detects a position-detecting magnetic field generated by the capsule endoscope 10, and a computing device 40 which performs a computation process, such as position detection, of the capsule endoscope 10 based on a detection signal of the position-detecting magnetic field output from the magnetic field detection device 30. In addition, the position detection system 1 may further include a receiving device 50 which receives a signal wirelessly transmitted from the capsule endoscope 10 via a receiving antenna 51a pasted on a body surface of the subject 20, and a display device 60 which displays an image output from the computing device 40 and position information of the capsule endoscope 10, and the like.

Figure 2:
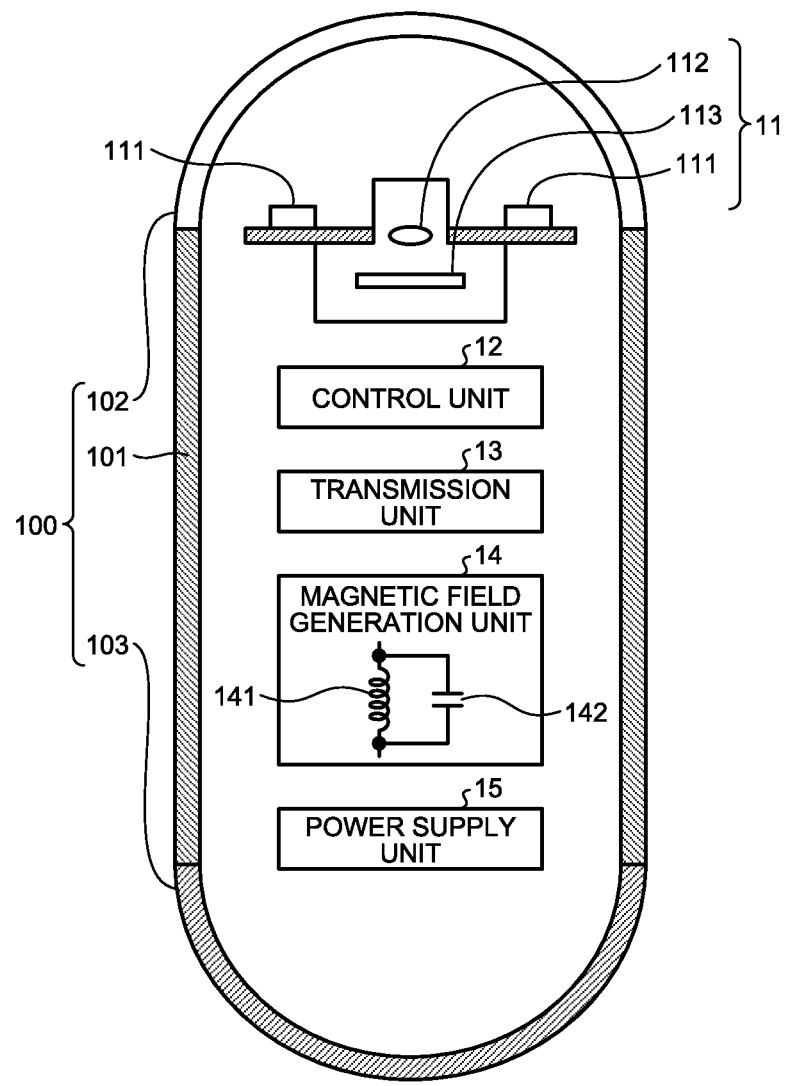
FIG. 2 is a schematic view illustrating an example of an internal structure of a capsule endoscope illustrated in FIG. 1.

FIG. 2 is a schematic view illustrating an example of an internal structure of the capsule endoscope 10 illustrated in FIG. 1. As illustrated in FIG. 2, the capsule endoscope 10 includes a casing 100 which is a capsule type formed in a shape that is easily introduced into the subject, an imaging unit 11 which is housed in the casing 100 and acquires an imaging signal by imaging the inside of the subject, a control unit 12 which controls various operations of the capsule endoscope 10 including the imaging unit 11 and executes predetermined signal processing with respect to an imaging signal acquired by the imaging unit 11, a transmission unit 13 which wirelessly transmits the imaging signal that has been subjected to the signal processing, a magnetic field generation unit 14 which generates an alternating magnetic field as a position-detecting magnetic field of the capsule endoscope 10, and a power supply unit 15 which supplies power to each unit of the capsule endoscope 10.

The casing 100 is an outer casing which is formed in a size that can be introduced into an organ of the subject. The casing 100 includes a tubular casing 101 which has a cylindrical shape and dome-shaped casings 102 and 103 each of which has a dome shape and is implemented by occluding both aperture ends of the tubular casing 101 by the dome-shaped casings 102 and 103 formed in the dome shape. The tubular casing 101 is formed using a colored member which is substantially opaque with respect to visible light. In addition, at least one (the dome-shaped casing 102 on the imaging unit 11 side in FIG. 2) of the dome-shaped casings 102 and 103 is formed using an optical member transparent with respect to light with a predetermined wavelength band such as the visible light. Incidentally, the single imaging unit 11 is provided only to the one dome-shaped casing 102 side in FIG. 2, but the two imaging units 11 may be provided. In this case, the dome-shaped casing 103 is also formed using the transparent optical member. The casing 100 configured in this manner includes the imaging unit 11, the control unit 12, the transmission unit 13, the magnetic field generation unit 14, and the power supply unit 15 in a liquid-tight manner.

The imaging unit 11 includes an illumination unit 111 such as an LED, an optical system 112 such as a condenser lens, and an image sensor 113 such as a CMOS image sensor and a CCD. The illumination unit 111 generates illumination light, such as white light, in an imaging field of view of the image sensor 113 and illuminates the subject inside the imaging field of view over the dome-shaped casing 102. The optical system 112 condenses reflection light from the imaging field of view on an imaging surface of the image sensor 113 to form an image. The image sensor 113 converts the reflection light (optical signal) from the imaging field of view received on the imaging surface into an electrical signal and outputs the converted signal as an image signal.

The control unit 12 operates the imaging unit 11 at a predetermined imaging frame rate and causes the illumination unit 111 to generate light in synchronization with an imaging frame rate. In addition, the control unit 12 generates image data by executing A/D conversion and other predetermined signal processing with respect to the imaging signal generated by the imaging unit 11. Further, the control unit 12 causes the magnetic field generation unit 14 to generate the alternating magnetic field by supplying power from the power supply unit 15 to the magnetic field generation unit 14.

The transmission unit 13 includes a transmission antenna, executes modulation processing by acquiring image data, which has been subjected to the signal processing by the control unit 12, and related information, and sequentially transmits the processed data and information to the outside via the transmission antenna in a wireless manner.

The magnetic field generation unit 14 includes a magnetic field generation coil 141, which forms a part of a resonant circuit and generates a magnetic field when a current flows, and a capacitor 142 which forms the resonant circuit together with the magnetic field generation coil 141, and generates the alternating magnetic field with a predetermined frequency, as the position-detecting magnetic field, by receiving the power supplied from the power supply unit 15.

The power supply unit 15 is a power storage unit, such as a button-type battery and a capacitor, and includes a switch unit such as a magnetic switch and an optical switch. When configured to include the magnetic switch, the power supply unit 15 switches on and off states of a power supply depending on the magnetic field applied from the outside and suitably supplies the power of the power storage unit to the respective components (the imaging unit 11, the control unit 12, and the transmission unit 13) of the capsule endoscope 10 in the on state. In addition, the power supply unit 15 stops the power supply to the respective components of the capsule endoscope 10 in the off state.

Referring to FIG. 1 again, the bed 21 includes a base portion 22 which allows the subject 20 to lie down thereon and a bed frame 23 which supports the base portion 22. The bed frame 23 needs to have strength, and thus, is formed using metal in the first embodiment.

Figure 3:
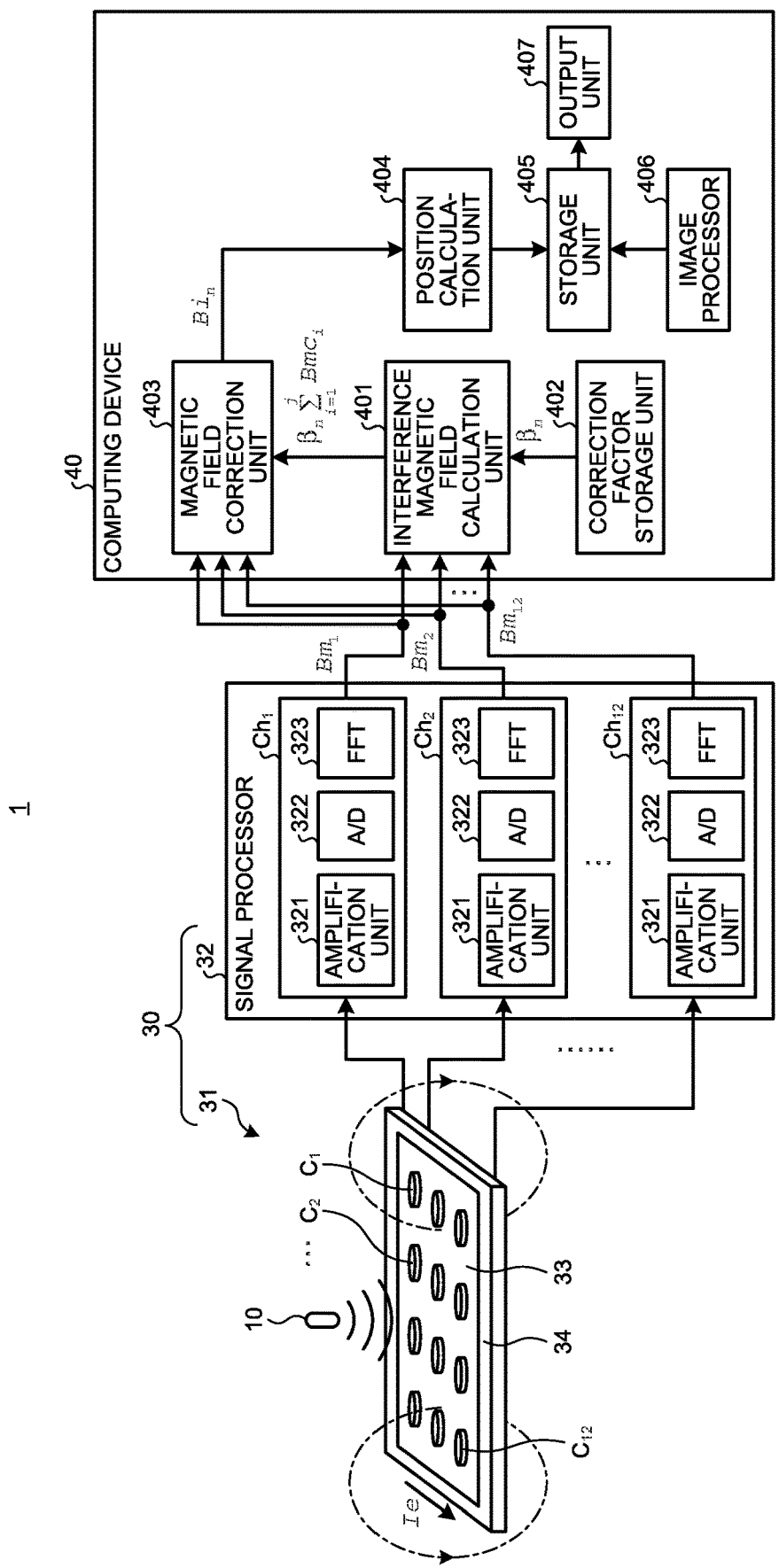
FIG. 3 is a diagram illustrating a configuration example of the position detection system according to the first embodiment of the disclosure.

FIG. 3 is a diagram illustrating a configuration example of the position detection system according to the first embodiment of the disclosure. The magnetic field detection device 30 includes a coil unit 31 in which a plurality of detection coils $C_n$ are arranged and a signal processor 32 which processes a detection signal output from each of the detection coils $C_n$. Herein, the subscript n is a number indicating each detection coil, and n=1 to 12 in FIG. 3.

Each of the detection coils $C_n$ is formed using a tubular coil obtained by winding a coil wire material in a coil spring shape, and has a size, for example, such that an aperture diameter thereof is about 30 to 40 mm, and a height thereof is about 5 mm. Each of the detection coils $C_n$ generates a current depending on a magnetic field distributed at each own position, and outputs the current to the signal processor 32 as the detection signal of the magnetic field.

These detection coils $C_n$ are arranged on a main surface of a panel 33 which is formed using a non-metal material such as resin and has a planar shape. In addition, a metal frame 34 to support the panel 33 may be provided at an outer circumference of the panel 33.

A region in which the position of the capsule endoscope 10 can be detected by the coil unit 31 is a detection target region R. The detection target region R is a three-dimensional region including a range in which the capsule endoscope 10 is movable inside the subject 20 and is set, in advance, depending on the arrangement of the plurality of detection coils $O_n$ and the intensity of the position-detecting magnetic field generated by the magnetic field generation unit 14 inside the capsule endoscope 10.

The signal processor 32 includes a plurality of signal processing channels $Ch_n$ where each signal processing channel $Ch_n$ corresponds to each detection coil $C_n$. Each of the signal processing channels $Ch_n$ includes an amplification unit 321 which amplifies the detection signal output from the detection coil $C_n$, an A/D conversion unit (A/D) 322 which performs digital conversion on the amplified detection signal, and an FFT processor (FFT) 323 which executes high-speed Fourier transform processing with respect to the digitally converted detection signal, and outputs a measurement value of the detection signal.

The computing device 40 is configured using a general purpose computer, for example, a personal computer, a work station, and the like, and executes a computation process of detecting a position and a posture of the capsule endoscope 10 based on the detection signal of the position-detecting magnetic field output from the signal processor 32 and a computation process of generating an image inside the subject 20 based on the image signal received through the receiving device 50.

To be specific, the computing device 40 includes an interference magnetic field calculation unit 401 which calculates an interference magnetic field generated from a member (magnetic field generation material) and serving as an interference source of the position-detecting magnetic field, a correction factor storage unit 402 which stores a correction factor used for correction of a measurement value of the position-detecting magnetic field detected by each of the detection coils $C_n$, a magnetic field correction unit 403 which corrects the measurement value of the position-detecting magnetic field detected by each of the detection coils $C_n$, and a position calculation unit 404 which calculates at least one of the position and the posture of the capsule endoscope 10 based on the corrected measurement value. Among them, the correction factor storage unit 402 stores the plurality of correction factors according to positions of the detection coils $C_n$ each of which is applied for each of measurement values output from the signal processing channels $Ch_n$.

In addition, the computing device 40 further includes a storage unit 405 which stores information relating to the position and the posture of the capsule endoscope 10 calculated by the position calculation unit 404 and the like, an image processor 406 which generates image data by executing predetermined image processing with respect to the image signal wirelessly transmitted from the capsule endoscope 10 and received by the receiving device 50 (see FIG. 1), and an output unit 407 which outputs the information and the image data relating to the position and the posture stored in the storage unit 405. Hereinafter, the information relating to the position and the posture of the capsule endoscope 10 is simply referred to also as position information.

The storage unit 405 is implemented using a recording medium and a write and read device, such as a flash memory and a hard disk, in which information is saved in a rewritable manner. The storage unit 405 stores various programs and various parameters to control the respective units of the computing device 40, a position detection operation program and an image processing program of the capsule endoscope 10 in addition to the position information and the image data described above.

The receiving device 50 acquires the image signal and the related information by selecting the receiving antenna 51a having the highest reception intensity with respect to a radio signal transmitted from the capsule endoscope 10 among the plurality of receiving antennas 51$a$ pasted on a body surface of the subject at the time of performing inspection using the capsule endoscope 10, and executing demodulation processing and the like with respect to the radio signal received via the selected receiving antenna 51$a$.

The display device 60 includes various displays, such as a liquid crystal and an organic EL, and displays information, such as an in-vivo image of the subject and a position and a direction of the capsule endoscope 10, on a screen based on the position information and the image data generated in the computing device 40.

Next, a method of correcting the measurement value in the position detection method according to the first embodiment will be described. A case is considered where the capsule endoscope 10 is present at an arbitrary position inside the detection target region R. When metallic members, which can be regarded as a loop coil (closed circuit), is present within a range that the position-detecting magnetic field generated from the capsule endoscope 10 is reachable, the position-detecting magnetic field penetrates through the region where those members exist, thereby generating a magnetic field. This magnetic field is detected by the detection coil $C_n$ together with the position-detecting magnetic field, which makes the measurement value of the detection signal output from the magnetic field detection device 30 contain an error. For example, when the bed frame 23 and the metal frame 34 configure a closed circuit in FIG. 1, these metallic members function as the interference magnetic field generation source (magnetic field generation material) with respect to the position-detecting magnetic field.

Thus, the position detection system 1 corrects the detection error caused by the interference magnetic field generation source with respect to the measurement value output from the magnetic field detection device 30, and calculates the position and the posture of the capsule endoscope 10 based on the corrected measurement value.

To be specific, a current Ie generated in the interference magnetic field generation source is given based on the following Formula (1) using a sum ΣBs of magnetic fields interlinking with respect to the interference magnetic field generation source.

$$Ie = K \times \Sigma Bs \quad (1)$$

In Formula (1), the reference sign K is a coefficient that is set depending on a size and a resistance value of the interference magnetic field generation source. In addition, the reference sign Σ is a total sum sign.

When the current Ie flows in the interference magnetic field generation source, an interference magnetic field $Bc_n$ is generated at each position of the detection coils $C_n$. The interference magnetic field $Bc_n$ is given based on the following Formula (2) using a coefficient $\alpha(r_n)$ set depending on a distance $r_n$ between the detection coil $C_n$ and the interference magnetic field generation source.

$$Bc_n = \alpha(r_n) \times Ie$$

$$Bc_n = \alpha(r_n) \times K \times \Sigma Bs \quad (2)$$

From Formula (2), it is understood that the interference magnetic field $Bc_n$ at each position of the detection coils $C_n$ is proportional to the sum ΣBs of the magnetic fields interlinking the interference magnetic field generation source.

The sum ns of the magnetic fields interlinking the interference magnetic field generation source can be approximated as a sum of magnetic field components detected by the detection coils $C_n$ capable of detecting the magnetic field component in a direction parallel to a direction of an interference magnetic field generated from the interference magnetic field generation source (that is, a direction orthogonal to an aperture surface of the interference magnetic field generation source). Thus, when a magnetic field component parallel to the direction of the interference magnetic field is denoted by $Bmc_i$ with respect to the measurement value of the magnetic field obtained by the respective detection coils $C_n$, the interference magnetic field $Bc_n$ is given based on the following Formula (3).

$$Bc_n = \alpha(r_n) \cdot K \cdot \sum_{i=1}^{j} Bmc_i \quad (3)$$

In Formula (3), an end value j of the sum is a total number of the detection coils $C_n$, and j=12 in FIG. 3.

In addition, the measurement value $Bm_n$ of the magnetic field detected by each of the detection coils $C_n$ in the middle of executing detection of the position of the capsule endoscope 10 is a sum of ideal value $Bi_n$ of the position-detecting magnetic field and the interference magnetic field $Bc_n$ at the position of the detection coil $C_n$. Accordingly, the following relationship of Formula (4) is established.

$$Bm_n = Bi_n + Bc_n$$

$$Bi_n = Bm_n - Bc_n \quad (4)$$

When Formula (3) is substituted for Formula (4), the following Formula (5) is obtained. In Formula (5), the coefficient $\alpha(r_n) \times K$ in Formula (3) is substituted by the correction factor $\beta_n$.

$$Bi_n = Bm_n - \beta_n \cdot \sum_{i=1}^{j} Bmc_i \quad (5)$$

Based on Formula (5), the ideal value $Bi_n$ of the position-detecting magnetic field of the capsule endoscope 10 at each position of the detection coils $C_n$ can be calculated using the measurement value $Bm_n$ of the magnetic field at the position of the detection coil $C_n$, the correction factor $\beta_n$, and the sum $\Sigma Bmc_i$ of the magnetic field components parallel to the direction of the interference magnetic field among the magnetic fields detected by the detection coils $C_n$.

On the contrary, when the ideal value $Bi_n$ of the position-detecting magnetic field has been already known, the correction factor $\beta_n$ is given based on the following Formula (6) obtained by deforming the Formula (5).

$$\beta_n = \frac{Bm_n - Bi_n}{\sum_{i=1}^{j} Bmc_i} \quad (6)$$

That is, the correction factor $\beta_n$ is a function with respect to the ideal value $Bi_n$ and the measurement value $Bm_n$.

Figure 4:
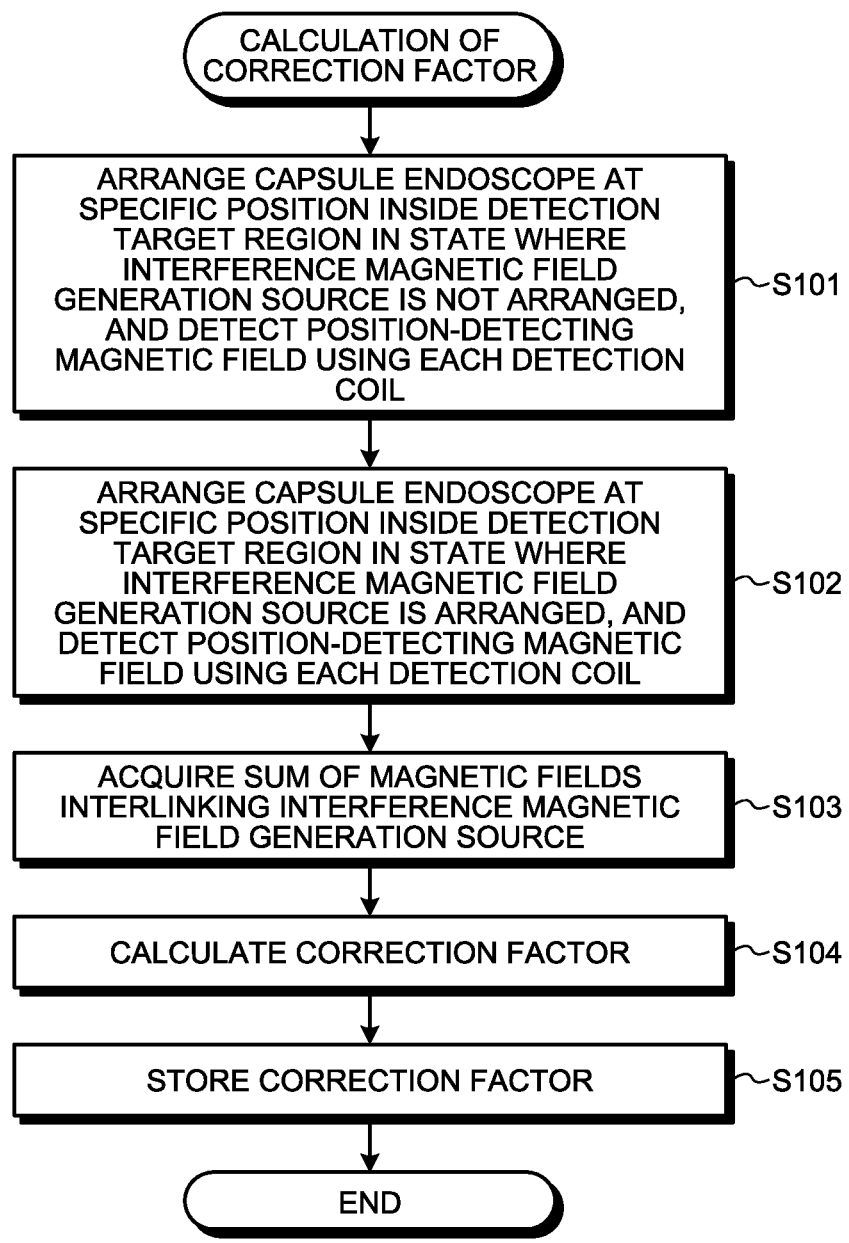
FIG. 4 is a flowchart illustrating a method of calculating a correction factor according to the first embodiment of the disclosure.

In the first embodiment, the above-described correction factor $\beta_n$ is calculated in advance, and is stored in the correction factor storage unit 402. FIG. 4 is a flowchart illustrating a method of calculating the correction factor $\beta_n$.

First, the capsule endoscope 10 is arranged at a specific position inside the detection target region R in a state where the interference magnetic field generation source is not arranged, and the capsule endoscope 10 is caused to generate the position-detecting magnetic field to detect the position-detecting magnetic field using each of the detection coils $C_n$ in Step S101. The measurement value of the position-detecting magnetic field at this time is set as the ideal value $Bi_n$ of the position-detecting magnetic field at each position of the detection coils $C_n$. Alternatively, the ideal value $Bi_n$ may be calculated based on a distance between the capsule endoscope 10 and each of the detection coils $C_n$.

Subsequently, the capsule endoscope 10 is arranged at the specific position inside the detection target region R (the same position as that in Step S101) in a state where the interference magnetic field generation source is arranged, and the capsule endoscope 10 is caused to generate the position-detecting magnetic field to detect the position-detecting magnetic field using each of the detection coils $C_n$ in Step S102. The measurement value of the position-detecting magnetic field at this time is set as the measurement value $Bm_n$ of the magnetic field at each position of the detection coils $C_n$.

Subsequently, the sum of the magnetic fields interlinking the interference magnetic field generation source is acquired in Step S103. To be specific, the magnetic field components parallel to the direction of the interference magnetic field are extracted from the measurement values $Bm_n$ of the magnetic fields detected by the detection coils $C_n$, and the sum $\Sigma Bmc_i$ of these magnetic field components is calculated. In FIG. 3, the aperture surface of the metal frame 34 and each aperture surface of the detection coils $C_n$ are arranged in parallel. Thus, the sum of the measurement values of the magnetic field detected by the respective detection coils $C_n$ may be calculated.

Subsequently, in Step S104, the correction factor $\beta_n$, which is given based on Formula (6), is calculated using the ideal value $Bi_n$, the measurement value $Bm_n$, and the sum $\Sigma Bmc_i$ of the magnetic field components, acquired in Steps S101 to S103.

Subsequently, the correction factor $\beta_n$ is stored in the correction factor storage unit 402 (see FIG. 3) in Step S105. Accordingly, the calculation of the correction factor is completed.

Figure 5:
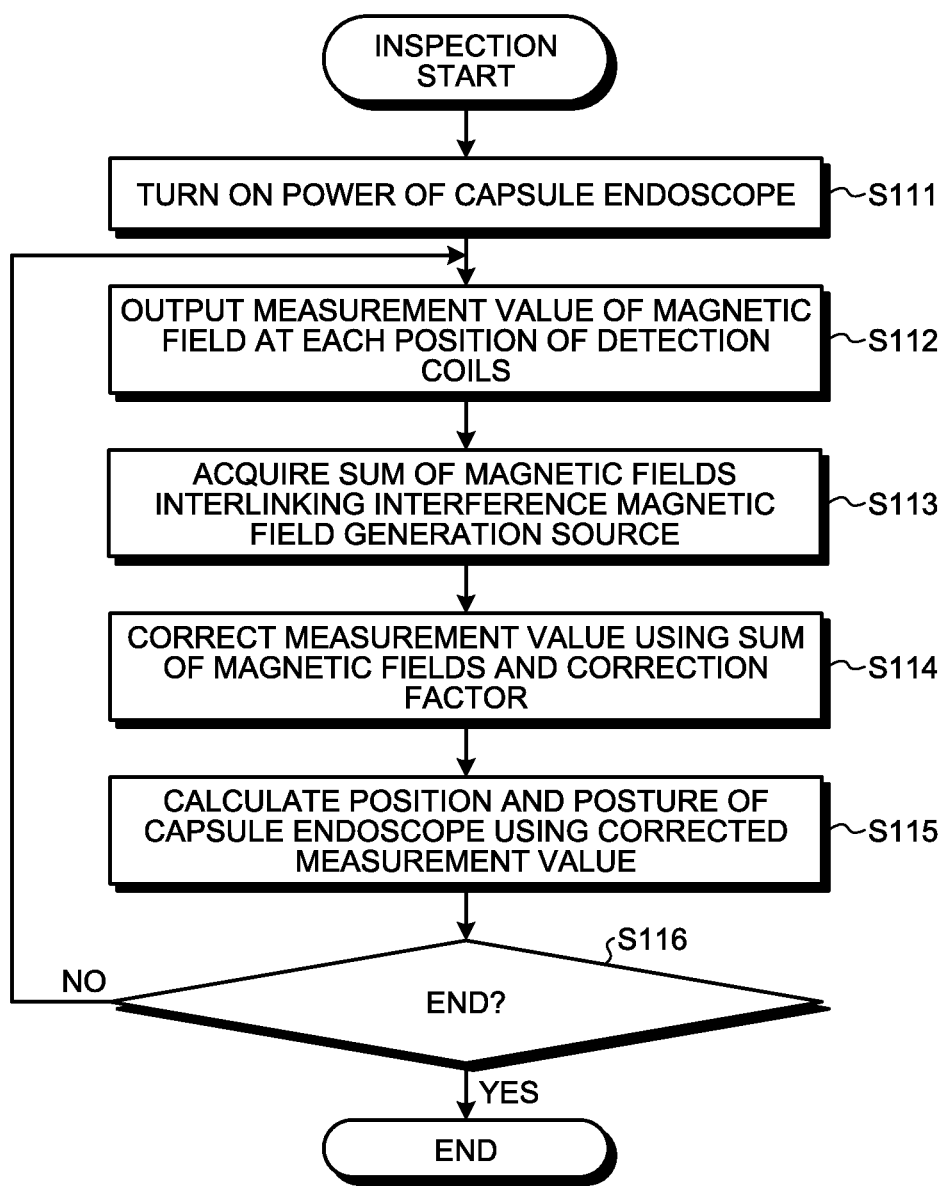
FIG. 5 is a flowchart illustrating a position detection method according to the first embodiment of the disclosure.

Next, the position detection method according to the first embodiment will be described. FIG. 5 is a flowchart illustrating the position detection method according to the first embodiment.

First, power of the capsule endoscope 10 is turned on in Step S111. Accordingly, the power supply from the power supply unit 15 (see FIG. 2) to the respective units of the capsule endoscope 10 is started so that the imaging unit 11 starts the imaging, and further, the magnetic field generation unit 14 starts the generation of the position-detecting magnetic field. In this state, the capsule endoscope 10 is introduced into the subject 20.

Subsequently, the magnetic field detection device 30 detects the position-detecting magnetic field generated by the capsule endoscope 10, and outputs the measurement value $Bm_n$ of the magnetic field at each position of the detection coils $C_n$ in Step S112. To be specific, each of the detection coils $C_n$ outputs the detection signal of the magnetic field, and the corresponding signal processing channel $Ch_n$ performs amplification, A/D conversion, and FFT processing with respect to the detection signal and outputs the processed signal to the computing device 40. The measurement value $Bm_n$ output from each of the signal processing channels $Ch_n$ is input to the interference magnetic field calculation unit 401 and the magnetic field correction unit 403.

Subsequently, the interference magnetic field calculation unit 401 acquires the sum of the magnetic fields interlinking the interference magnetic field generation source in Step S113. To be specific, the sum $\Sigma Bmc_i$ of the magnetic field components parallel to the direction of the interference magnetic fields extracted from the respective measurement values $Bm_n$ is calculated.

Subsequently, the magnetic field correction unit 403 acquires the measurement value $Bm_n$ of the magnetic field from the signal processor 32, and corrects the measurement value $Bm_n$ based on Formula (5) using the sum $\Sigma Bmc_i$ of the magnetic field components and the correction factor $\beta_n$ stored in the correction factor storage unit 402 in Step S114. The corrected measurement value $Bi_n$ is set as the ideal value of the position-detecting magnetic field at the each position of the detection coils $C_n$.

Subsequently, in Step S115, the position calculation unit 404 calculates the position and the posture of the capsule endoscope 10 using the measurement value (the ideal value $Bi_n$) corrected in Step S114. The calculated information on the position and the posture of the capsule endoscope 10 is stored in the storage unit 405.

Subsequently, the computing device 40 determines whether to end the position detection operation of the capsule endoscope 10 in Step S116. To be specific, the computing device 40 determines to end the inspection in a case where the transmission of the radio signal from the capsule endoscope 10 has stopped, a predetermined time has elapsed from the power-on of the capsule endoscope 10 and the computing device 40 has been operated to end the operation of the computing device 40.

When it is determined not to end the position detection operation (Step S116: No), the operation of the position detection system 1 returns to Step S112. On the contrary, when it is determined to end the position detection operation (Step S116: Yes), the operation of the position detection system 1 is ended.

As described above, the capsule endoscope 10 is arranged at the specific position inside the detection target region R to generate the position-detecting magnetic field, and each detection of the position-detecting magnetic field is performed in the state where the interference magnetic field generation source is arranged and in the state where the interference magnetic field generation source is not arranged according to the first embodiment of the disclosure. Thus, when these detection results are used, it is possible to acquire the correction factor $\beta_n$ indicating a relationship between the measurement value of the position-detecting magnetic field that contains the interference magnetic field and the ideal value of the magnetic field for detection that does not contain the interference magnetic field. Accordingly, when the correction factor $\beta_n$ and the sum $\Sigma Bmc_i$ of the magnetic field component calculated from the measurement value of the position-detecting magnetic field are used, it is possible to perform the highly accurate correction with respect to the measurement value. Accordingly, it is possible to exclude the influence of the interference magnetic field and accurately calculate the position and the posture of the capsule endoscope 10.

In addition, the correction factor $\beta_n$ is acquired for each of the detection coils $C_n$ according to the first embodiment of the disclosure. Thus, it is possible to perform the highly accurate correction in a spatially continuous manner according to the position of the detection coil $C_n$ regardless of the position or the posture of the capsule endoscope 10.

Further, it is possible to detect a wide range of magnetic fields by increasing the total number of the detection coils $C_n$ and the signal processing channels $Ch_n$ according to the first embodiment of the disclosure. Accordingly, it is possible to improve the accuracy in detection of the position and the posture of the capsule endoscope 10 while suppressing an increase in computation amount.

Incidentally, the correction factor $\beta_n$ is calculated using Formula (6) in the first embodiment, but the correction factor $\beta_n$ may be calculated based on FEM analysis using the measurement value of the position-detecting magnetic field obtained by preliminary measurement (see Steps S101 and S102 in FIG. 4).

Second Embodiment

Figure 6:
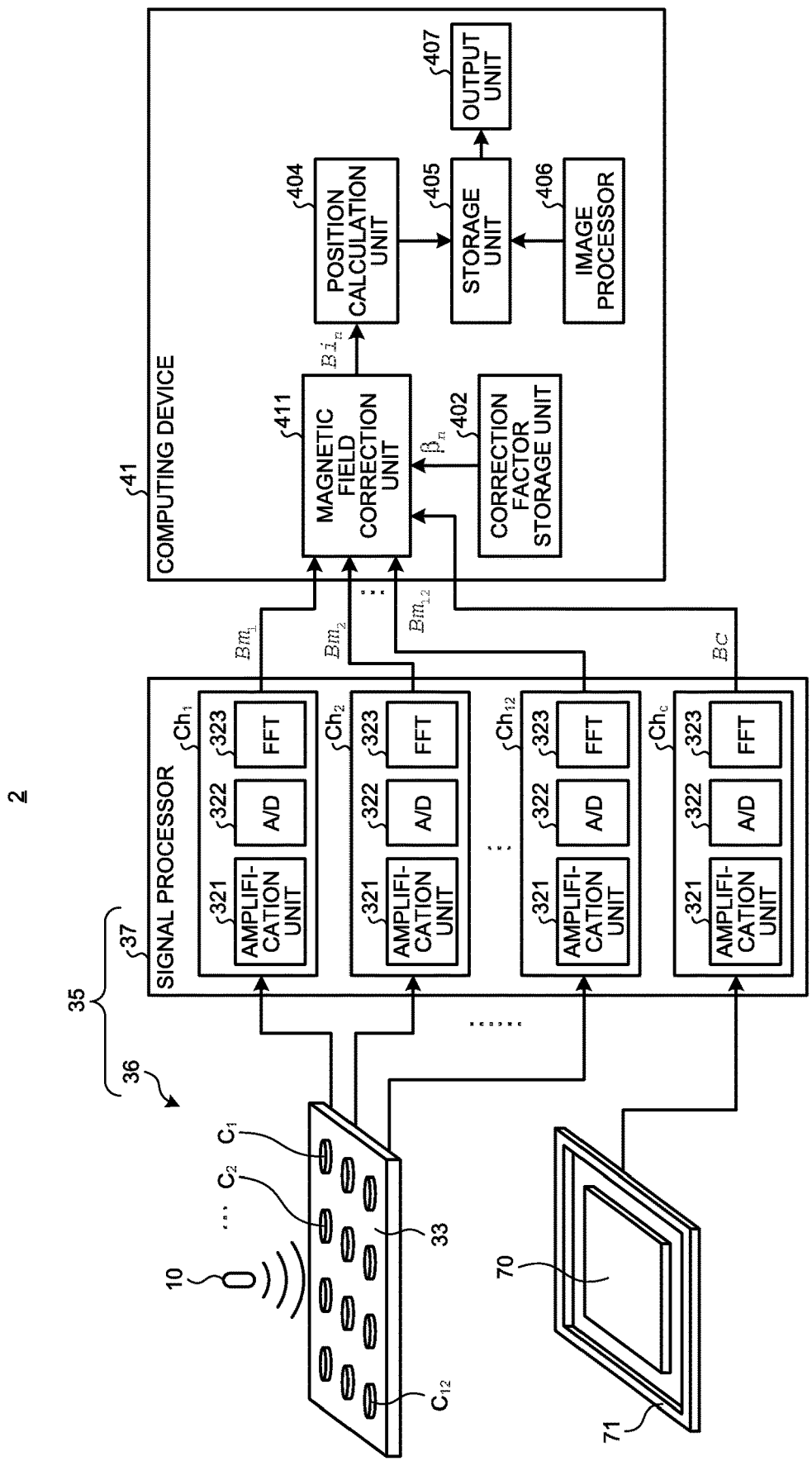
FIG. 6 is a diagram illustrating a configuration example of a position detection system according to a second embodiment of the disclosure.

Next, a second embodiment of the disclosure will be described. FIG. 6 is a diagram illustrating a configuration example of a position detection system according to a second embodiment of the disclosure. As illustrated in FIG. 6, a position detection system 2 according to the second embodiment is provided with a magnetic field detection device 35 which includes a coil unit 36 and a signal processor 37, a computing device 41, an interference magnetic field generation source 70 which is provided in the vicinity of the coil unit 36, and an interference magnetic field detector 71 which is provided around the interference magnetic field generation source 70. Among these, a configuration and an operation of the coil unit 36 are the same as those of the coil unit 31 illustrated in FIG. 3.

The interference magnetic field generation source 70 is formed using, for example, a metallic plate. An eddy current is generated as a position-detecting magnetic field generated from the capsule endoscope 10 penetrates through the interference magnetic field generation source 70, and an interference magnetic field is generated due to the eddy current. For example, when a metallic support member or the like is used for the bed 21 on which the subject 20 is placed, this support member or the like becomes the interference magnetic field generation source 70.

The interference magnetic field detector 71 is a member whose reactant has been increased by connecting a resistor to a coil, for example, and is wound along an outer circumference of the interference magnetic field generation source 70. The interference magnetic field detector 71 outputs the current, which flows to the coil due to action of the interference magnetic field generated by the interference magnetic field generation source 70, to the signal processor 37 as a detection signal of the interference magnetic field.

The signal processor 37 includes a plurality of signal processing channels $Ch_n$, which corresponds, respectively, to a plurality of detection coils $C_n$ provided in the coil unit 36 and a signal processing channel $Ch_c$ that processes the detection signal of the interference magnetic field output from the interference magnetic field detector 71. Each of the signal processing channels includes the amplification unit 321 which amplifies the detection signal of the interference magnetic field, the A/D conversion unit (A/D) 322 which performs digital conversion on the amplified detection signal, and the FFT processor (FFT) 323 which executes high-speed Fourier transform processing with respect to the digitally converted detection signal.

The computing device 41 includes a magnetic field correction unit 411 instead of the interference magnetic field calculation unit 401 and the magnetic field correction unit 403, which is different from the computing device 40 illustrated in FIG. 3. A configuration and an operation of each unit of the computing device 41, except for the magnetic field correction unit 411, are the same as those according to the first embodiment.

Next, a method of calculating a correction factor in a position detection method according to the second embodiment of the disclosure will be described. The position detection method according to the second embodiment is the same as the first embodiment on the whole, but is different from the first embodiment in that the interference magnetic field detected by the interference magnetic field detector 71 is used in the process of calculating the correction factor illustrated in FIG. 4 and a process of correcting the measurement value illustrated in FIG. 5 instead of the sum $\Sigma Bmc_i$ of the magnetic field component parallel to the direction of the interference magnetic field among the magnetic fields detected by the detection coils $C_n$.

At the time of calculating the correction factor $\beta_n$, a measurement value $Bc$ of the interference magnetic field detected by the interference magnetic field detector 71, that is, an output value of the signal processing channel $Ch_c$ is acquired together with the ideal value $Bi_n$ of the position-detecting magnetic field detected by each of the detection coils $C_n$ in Step S101 and the measurement value $Bm_n$ of the position-detecting magnetic field detected by each of the detection coils $C_n$ in Step S102, in the second embodiment. Further, the correction factor $\beta_n$ given based on the following Formula (7) is calculated using these values (see Step S104), and is stored in the correction factor storage unit 402 in advance.

$$\beta_n = \frac{Bm_n - Bi_n}{Bc} \quad (7)$$

In addition, the measurement value $Bm_n$ of the position-detecting magnetic field detected by each of the detection coils $C_n$ in Step S112, and the measurement value $Bc$ of the interference magnetic field detected by the interference magnetic field detector 71 are acquired at the time of performing the position detection of the capsule endoscope 10 in the second embodiment. Further, the correction value (the ideal value) $Bi_n$ of the position-detecting magnetic field, which is given based on Formula (8), is calculated using the measurement value $Bm_n$, the measurement value $Bc$ of the interference magnetic field, and the correction factor $\beta_n$ stored in the correction factor storage unit 402.

$$Bi_n = Bm_n - \beta_n \cdot Bc \quad (8)$$

As described above, the correction factor $\beta_n$ is calculated based on the measurement value of the interference magnetic field detected by the interference magnetic field detector 71, and the correction value $Bi_n$ of the position-detecting magnetic field is calculated according to the second embodiment of the disclosure. Thus, it is possible to reduce the computation amount as compared to the first embodiment.

MODIFIED EXAMPLE

Next, a modified example of the second embodiment of the disclosure will be described. When the metal frame 34 is provided in the coil unit 31 as in the first embodiment (see FIG. 3), an interference magnetic field generated from the metal frame 34 may be directly detected by the interference magnetic field detector 71 by arranging the interference magnetic field detector 71 around the metal frame 34. In this case, the calculation of the correction factor $\beta_n$ and the correction of the measurement value of the position-detecting magnetic field are performed using the measurement value of the interference magnetic field detected by the interference magnetic field detector 71, which is similar to the above-described second embodiment. According to this modified example, it is unnecessary to calculate the sum $\Sigma Bmc_i$ of the magnetic field component parallel to the direction of the interference magnetic field, and thus, it is possible to reduce the computation amount.

Third Embodiment

Figure 7:
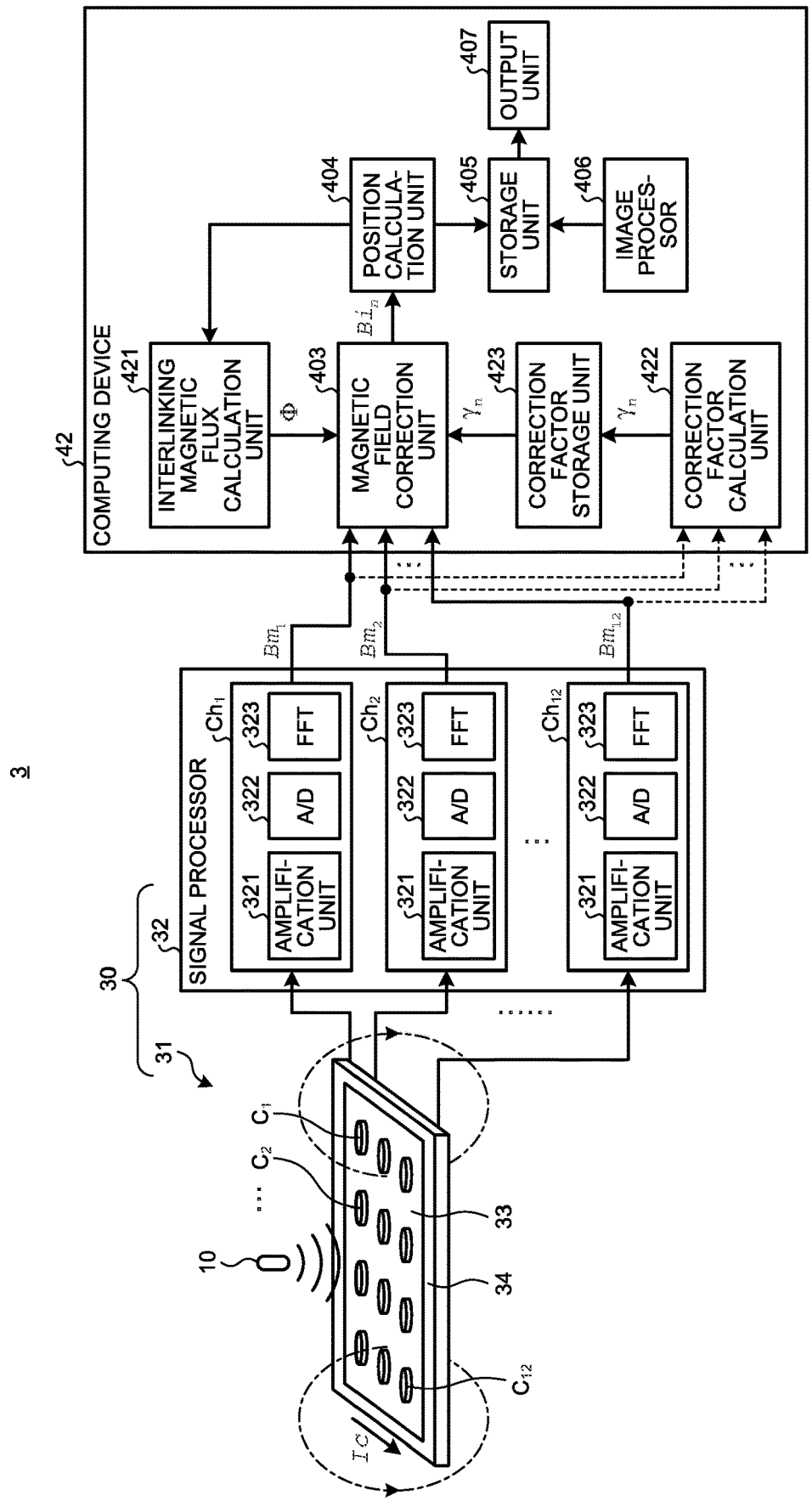
FIG. 7 is a diagram illustrating a configuration example of a position detection system according to a third embodiment of the disclosure.

Next, a third embodiment of the disclosure will be described. FIG. 7 is a diagram illustrating a configuration example of a position detection system according to the third embodiment of the disclosure. As illustrated in FIG. 7, a position detection system 3 according to the third embodiment includes the magnetic field detection device 30 and a computing device 42. Among these, the configuration and the operation of the magnetic field detection device 30 are the same as those according to the first embodiment.

The computing device 42 includes an interlinking magnetic flux calculation unit 421, a correction factor calculation unit 422, and a correction factor storage unit 423 instead of the interference magnetic field calculation unit 401 and the correction factor storage unit 402, which is different from the computing device 40 illustrated in FIG. 3.

The interlinking magnetic flux calculation unit 421 calculates an interlinking magnetic flux with respect to an interference magnetic field generation source generated by a position-detecting magnetic field, which is generated by the capsule endoscope 10, based on calculation results of the position and the posture of the capsule endoscope 10 obtained by immediately previous calculation of the position calculation unit 404.

The correction factor calculation unit 422 calculates a correction factor $\gamma_n$ which is used for correction of the measurement value $Bm_n$ of the position-detecting magnetic field detected by the detection coil $C_n$. The correction factor storage unit 423 stores the correction factor $\gamma_n$ calculated by the correction factor calculation unit 422.

Next, a method of correcting the measurement value in a position detection method according to the third embodiment will be described. As illustrated in FIG. 7, the metal frame 34 of the coil unit 31 can be regarded as a loop coil. In this case, an induced current Ic, which is generated in the metal frame 34 as the position-detecting magnetic field generated from the capsule endoscope 10 penetrates through an aperture of the metal frame 34, is given based on the following Formula (9) using a resistance $R_{frame}$ of the metal frame 34, an angular frequency $\omega$, and an interlinking magnetic flux $\Phi$.

$$Ic = \frac{1}{R_{frame}} \omega \Phi \qquad (9)$$

The interference magnetic field $Bc_n$ represented by the following Formula (10) is generated at each position of the detection coils $C_n$ due to the induced current Ic. In Formula (10), the coefficient $K(r_n)$ is a distribution function of a magnetic field set depending on a distance $r_n$ between the detection coil $C_n$ and the metal frame 34.

$$Bc_n = K(r_n) \cdot Ic = \frac{K(r_n)}{R_{frame}} \cdot \omega \Phi \qquad (10)$$

Further, the coefficient $\omega \cdot K(r_n)/R_{frame}$ is set as the correction factor $\gamma_n$, and this correction factor $\gamma_n$ is acquired by calibration which is performed before the inspection. Herein, since the measurement value $Bm_n$ of the position-detecting magnetic field at the position of the detection coil $C_n$ is the sum ($Bm_n=Bi_n+Bc_n$) of the ideal value $Bi_n$ of the position-detecting magnetic field and the interference magnetic field $Bc_n$ at the position of the detection coil $C_n$, a relationship of the following Formula (11) is established.

$$\gamma_n = \frac{Bm_n - Bi_n}{\Phi} \qquad (11)$$

In this case, the interference magnetic field $Bc_n$ ($Bc_n=Bm_n-Bi_n$) and the interlinking magnetic flux $\Phi$ at each position of the detection coils $C_n$ are acquired, and the correction factor $\gamma_n$, which is given based on Formula (11), is calculated using these values. That is, the correction factor $\gamma_n$ is a function of the ideal value $Bi_n$ and the measurement value $Bm_n$. The calculated correction factor $\gamma_n$ is stored in the correction factor storage unit 423.

The ideal value $Bi_n$ of the position-detecting magnetic field at the position of the detection coil $C_n$ is given based on the following Formula (12) using the correction factor $\gamma_n$ acquired in this manner and the interlinking magnetic field $\Phi$ during the position detection of the capsule endoscope 10.

$$Bi_n = Bm_n - \gamma_n \cdot \Phi \qquad (12)$$

Figure 8:
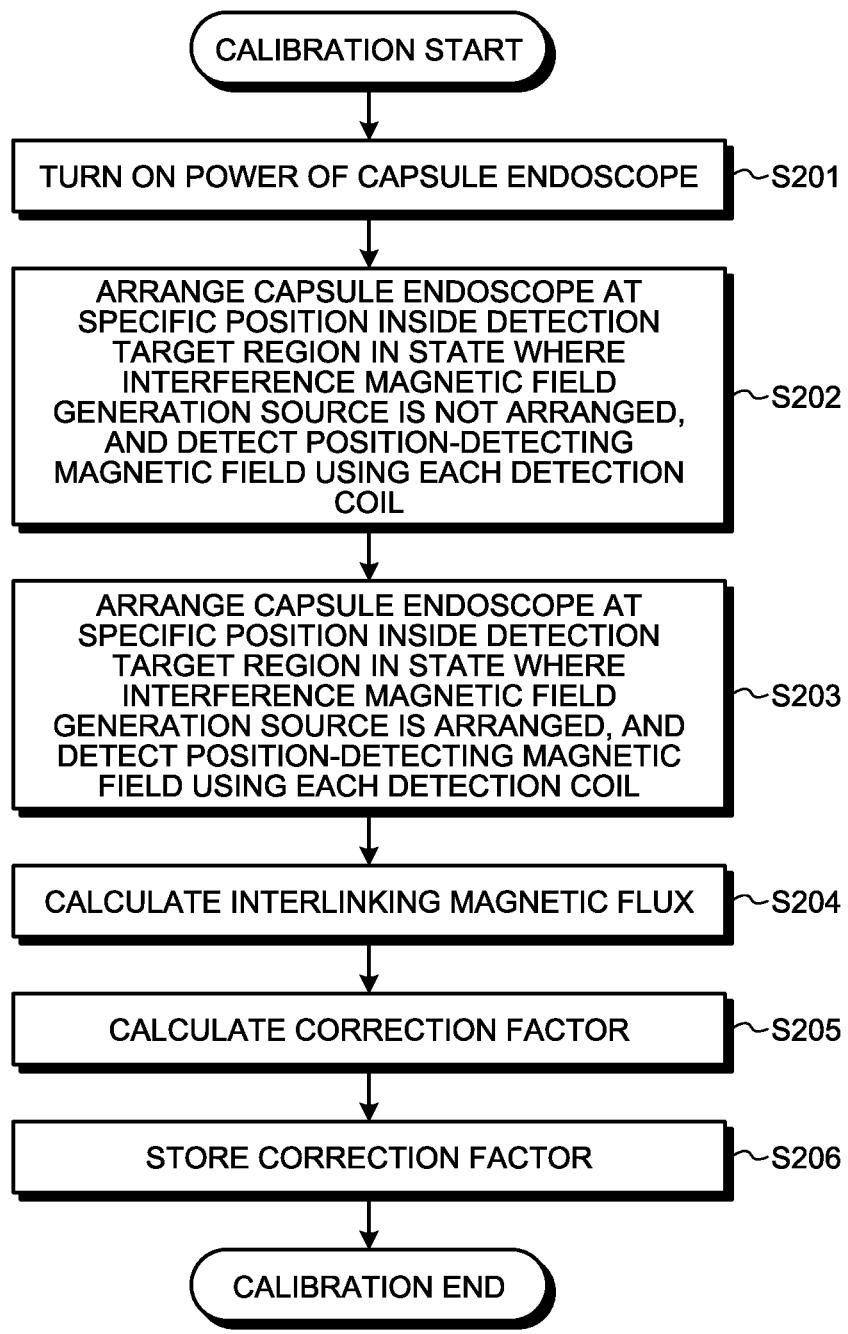
FIG. 8 is a flowchart illustrating a calibration process in a position detection method according to the third embodiment of the disclosure.

Next, a position detection method according to the third embodiment of the disclosure will be described. FIG. 8 is a flowchart illustrating a calibration process in the position detection method according to the third embodiment of the disclosure.

First, power of the capsule endoscope 10 is turned on in Step S201 illustrated in FIG. 8. Accordingly, the power supply from the power supply unit 15 (see FIG. 2) to the respective units of the capsule endoscope 10 is started so that the imaging unit 11 starts the imaging, and further, the magnetic field generation unit 14 starts the generation of the position-detecting magnetic field.

Subsequently, the capsule endoscope 10 is arranged at a specific position inside the detection target region R in a state where the interference magnetic field generation source is not arranged, and the position-detecting magnetic field is detected using each of the detection coils $C_n$ in Step S202. The measurement value at this time is set as the ideal value $Bi_n$ of the position-detecting magnetic field at each position of the detection coils $C_n$. During the calibration, these ideal values $Bi_n$ are input to the correction factor calculation unit 422. Alternatively, the ideal value $Bi_n$ may be theoretically calculated from the distance between the capsule endoscope 10 and each of the detection coils $C_n$.

Subsequently, the capsule endoscope 10 is arranged at the specific position inside the detection target region R (the same position as that in Step S202) in a state where the interference magnetic field generation source is arranged, and the position-detecting magnetic field is detected using each of the detection coils $C_n$ in Step S203. The measurement value at this time is set as the measurement value $Bm_n$ of the magnetic field at each position of the detection coils $C_n$. During the calibration, these measurement values $Bm_n$ are also input to the correction factor calculation unit 422.

Subsequently, the interlinking magnetic flux Φ is calculated based on a relationship in position and posture between the capsule endoscope 10 and the interference magnetic field generation source (for example, the metal frame 34) in Step S204. It is possible to apply various known methods as a method of calculating the interlinking magnetic flux Φ. For example, a method disclosed in Japanese Patent No. 4847520 will be described.

The position-detecting magnetic field generated from the capsule endoscope 10 can be regarded as a magnetic field generated by a magnetic dipole. A positional coordinate of the magnetic dipole is set as (x,y,z), a magnetic moment of the magnetic dipole is set as (Mx,My,Mz), and a vector formed of these parameters is set as a vector p=(x,y,z,Mx,My,Mz).

When the interference magnetic field generation source is regarded as a loop coil, it is possible to calculate a magnetic flux density $B_g(p)$ for a certain point on an aperture surface of the loop coil if a position and an orientation of the loop coil are set. This calculation is performed to obtain an electromotive force generated in the loop coil, and thus, the calculation is performed at as many points as possible to obtain an average value $B_g\_mean(p)$ of the magnetic flux density which is given based on the following Formula (13) Incidentally, an arrow is attached to the magnetic flux density and vector elements such as the vector p in the following Formulas (13) to (15).

$$\vec{B}_g\_mean(\vec{p}) = \frac{1}{N}\sum_{k=1}^{N}\vec{B}_g k(p) \quad (13)$$

The electromotive force generated in the loop coil is proportional to the number of turns, the area, and each frequency in relation to the average value $B_g\_mean(p)$ of the magnetic flux density. A current $I_c$, obtained by dividing the electromotive force by an inductance of the loop coil, flows in the loop coil. Accordingly, this current also becomes a function ($I_c(p)$) of the vector p.

When a size of the interference magnetic field generation source, which is regarded as the loop coil, is considered, the magnetic field generated from the loop coil is generally obtained by dividing the loop coil into a plurality of current elements and applying the Biot-Savart law without regarding the loop coil as the magnetic dipole.

When a position vector of the current element is set as $r_c$, a current vector of each current element is set as $d_c$, and a position vector of a position at which a magnetic field is detected is set as $r_{si}$, the magnetic field intensity $B_{ci}(p)$ at each position is given based on the following Formula (14).

$$\vec{B}_{ci}(\vec{p}) = \oint \mu_0 \frac{I_c(\vec{p}) \cdot \vec{d}_c \times (\vec{r}_{si} - \vec{r}_c)}{4\pi|\vec{r}_{si} - \vec{r}_c|^3} \quad (14)$$

Accordingly, it is possible to obtain the interlinking magnetic flux Φ by performing computation of Formula (14) for each position inside the aperture surface of the interference magnetic field generation source based on a coordinate of the specific position at which the capsule endoscope 10 is arranged, and performing computation of the following Formula (15).

$$\Phi = \int \vec{B}_{ci} \cdot d\vec{s} \quad (15)$$

Subsequently, the correction factor $\gamma_n$ which is given based on Formula (11), is calculated using the ideal value $Bi_n$, the measurement value $Bm_n$, and the interlinking magnetic flux Φ, acquired in Steps S202 to S204, in Step S205.

Subsequently, the correction factor $\gamma_n$ is stored in the correction factor storage unit 423 (see FIG. 7) in Step S206. Accordingly, the calibration is ended.

Figure 9:
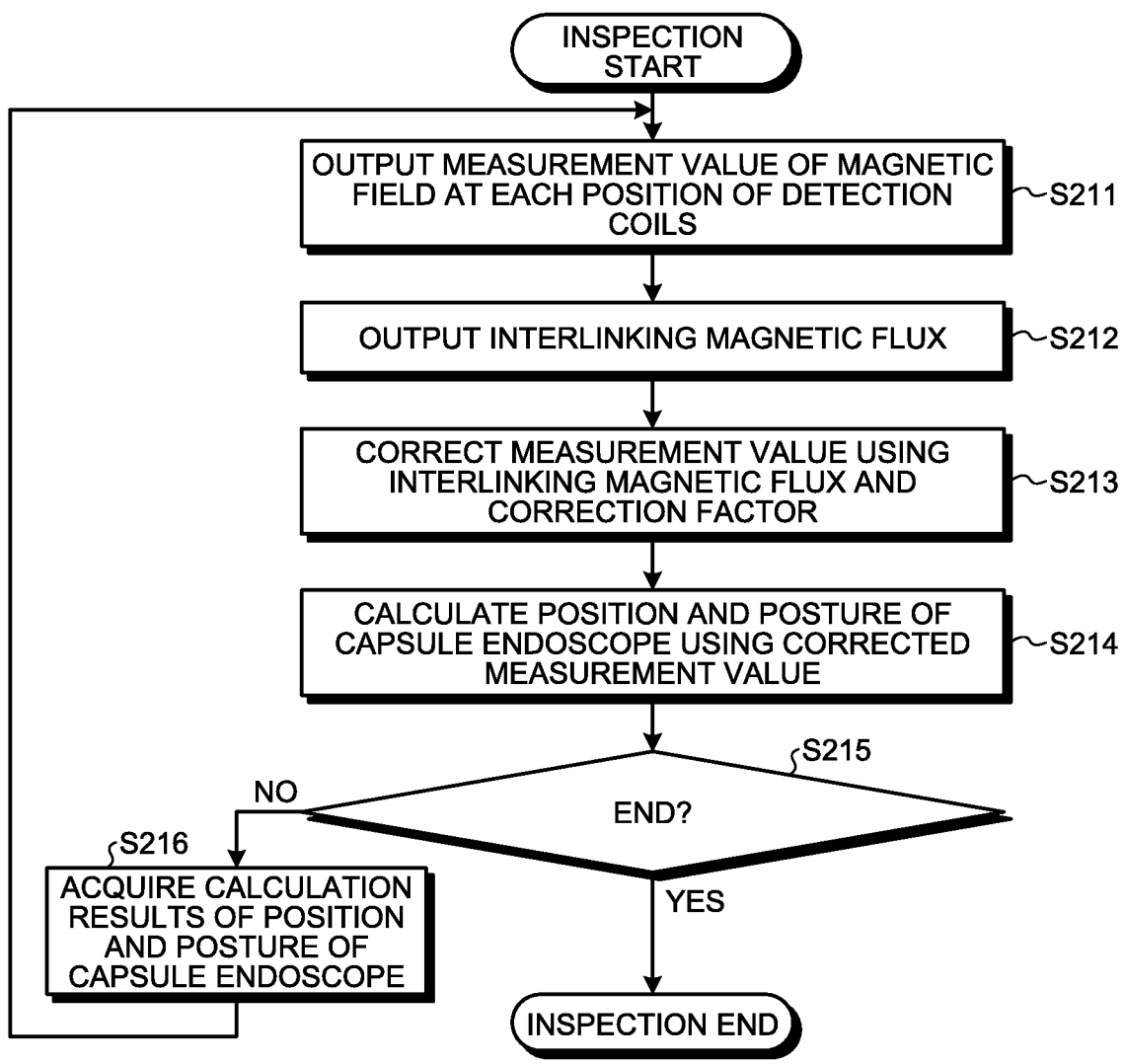
FIG. 9 is a flowchart illustrating the position detection method according to the third embodiment of the disclosure.

Thereafter, the capsule endoscope 10 is introduced into the subject 20 to start the inspection. FIG. 9 is a flowchart illustrating a position detection process during the inspection which is executed continuously to the calibration process in the position detection method according to the third embodiment of the disclosure.

In Step S211, the magnetic field detection device 30 detects the position-detecting magnetic field generated by the capsule endoscope 10, and outputs the measurement value $Bm_n$ of the magnetic field at each position of the detection coils $C_n$. During the inspection, these measurement values $Bm_n$ are input to the magnetic field correction unit 403.

Subsequently, in Step S212, the interlinking magnetic flux calculation unit 421 calculates the interlinking magnetic flux Φ based on the relationship between the position and the posture of the capsule endoscope 10 and the interference magnetic field generation source obtained in the immediately previous calculation. The method of calculating the interlinking magnetic flux Φ based on the position and the posture of the capsule endoscope 10 is the same as that in Step S204 (see Formula (15)).

Incidentally, in Step S212 for the first time at which the position detection operation of the capsule endoscope 10 has not been executed yet, the total sum $\Sigma Bmc_i$ of components parallel to the direction of the interference magnetic field among the measurement values $Bm_n$ of the position-detecting magnetic fields detected by the respective detection coils $C_n$ is used as the interlinking magnetic flux Φ.

Subsequently, the magnetic field correction unit 403 corrects the measurement value $Bm_n$ based on Formula (12) using the measurement value $Bm_n$ output from the signal processor 32, the interlinking magnetic flux Φ calculated by the interlinking magnetic flux calculation unit 421, and the correction factor $\gamma_n$ stored in the correction factor storage unit 423 in Step S213. The corrected measurement value $Bi_n$ is set as the ideal value of the position-detecting magnetic field at the each position of the detection coils $C_n$.

Subsequently, in Step S214, the position calculation unit 404 calculates the position and the posture of the capsule endoscope 10 using the corrected measurement value (the ideal value $Bi_n$). The calculated information on the position and the posture of the capsule endoscope 10 is stored in the storage unit 405.

Subsequently, the computing device 42 determines whether to end the position detection operation of the capsule endoscope 10 in Step S215. To be specific, the computing device 42 determines to end the inspection in a case where the transmission of the radio signal from the capsule endoscope 10 has stopped, a predetermined time has elapsed from the power-on of the capsule endoscope 10 and the computing device 42 has been operated to end the operation of the computing device 42.

When it is determined not to end the position detection operation (Step S215: No), the interlinking magnetic flux calculation unit 421 acquires calculation results of the position and the posture of the capsule endoscope 10 calculated in Step S214 (Step S216). Thereafter, the operation of the position detection system 3 returns to Step S211.

On the contrary, when it is determined to end the position detection operation (Step S215: Yes), the operation of the position detection system 3 is ended.

As described above, the interference magnetic field generation source is regarded as the loop coil, and the correction factor according to the characteristic of the interference magnetic field generation source is calculated according to the third embodiment of the disclosure. Thus, it is possible to perform the highly accurate correction.

In addition, the interlinking magnetic flux is calculated based on the position and the posture of the capsule endoscope 10 obtained in the immediately previous calculation, and the correction of the measurement value of the position-detecting magnetic field is performed using the interlinking magnetic flux according to the third embodiment of the disclosure. Thus, it is possible to perform the highly accurate correction in a spatially continuous manner regardless of the position or the posture of the capsule endoscope 10.

Fourth Embodiment

Figure 10:
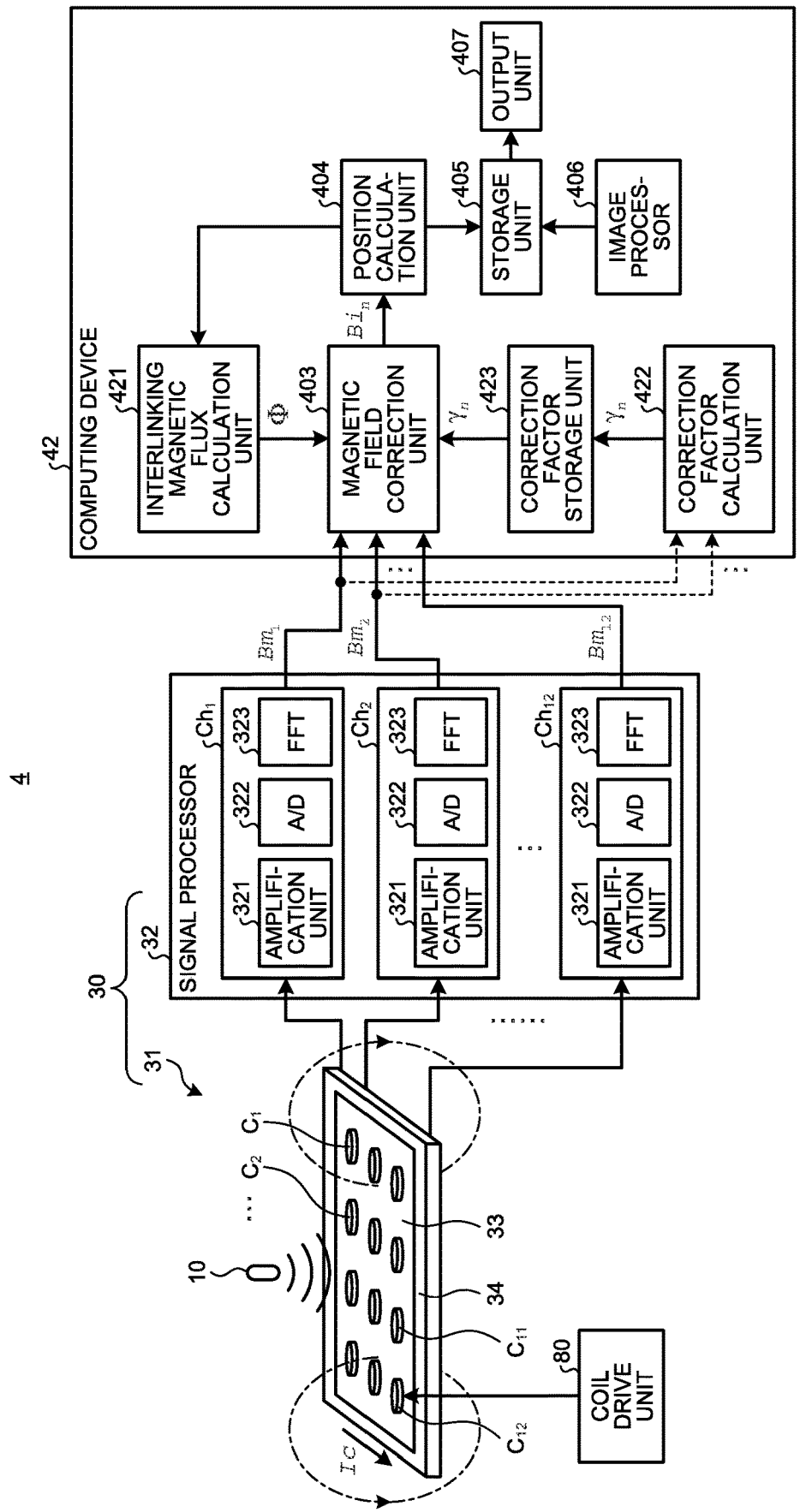
FIG. 10 is a diagram illustrating a configuration example of a position detection system according to a fourth embodiment of the disclosure.

Next, a fourth embodiment of the disclosure will be described. FIG. 10 is a diagram illustrating a configuration example of a position detection system according to the fourth embodiment of the disclosure. As illustrated in FIG. 10, a position detection system 4 according to the fourth embodiment further includes a coil drive unit 80 which supplies power to one detection coil to be driven among the plurality of detection coils $C_n$, which is different from the position detection system 3 illustrated in FIG. 7. In FIG. 10, a detection coil $C_{12}$ is used as a drive coil. Incidentally, the configuration and the operation of the magnetic field detection device 30 and the computing device 42 are the same as those in the third embodiment.

In the fourth embodiment, when the correction factor $\gamma_n$ is calculated by calibration (see FIG. 8), a magnetic field with a specific intensity is generated by supplying power from the coil drive unit 80 to the detection coil $C_{12}$ instead of arranging the capsule endoscope 10 inside the detection target region R to generate the position-detecting magnetic field. To be specific, it is preferable to make the magnetic field generated at the same degree as the position-detecting magnetic field generated by the capsule endoscope 10. Further, the magnetic field generated by the detection coil $C_{12}$ is regarded as the position-detecting magnetic field, and the correction factor $\gamma_n$ is calculated based on detection signals of magnetic fields detected by the other detection coils $C_1$ to $C_{11}$. Incidentally, a position detection method in the inspection using the capsule endoscope 10 is the same as that in the third embodiment (see FIG. 9).

It is unnecessary to use the capsule endoscope 10 in the calibration according to the fourth embodiment, and thus, it is possible to suppress power consumption of the power supply unit 15 built in the capsule endoscope 10. In addition, a position of the detection coil $C_{12}$ driven at the time of calibration is fixed according to the fourth embodiment, and thus, it is possible to perform the stable calibration.

Fifth Embodiment

Figure 11:
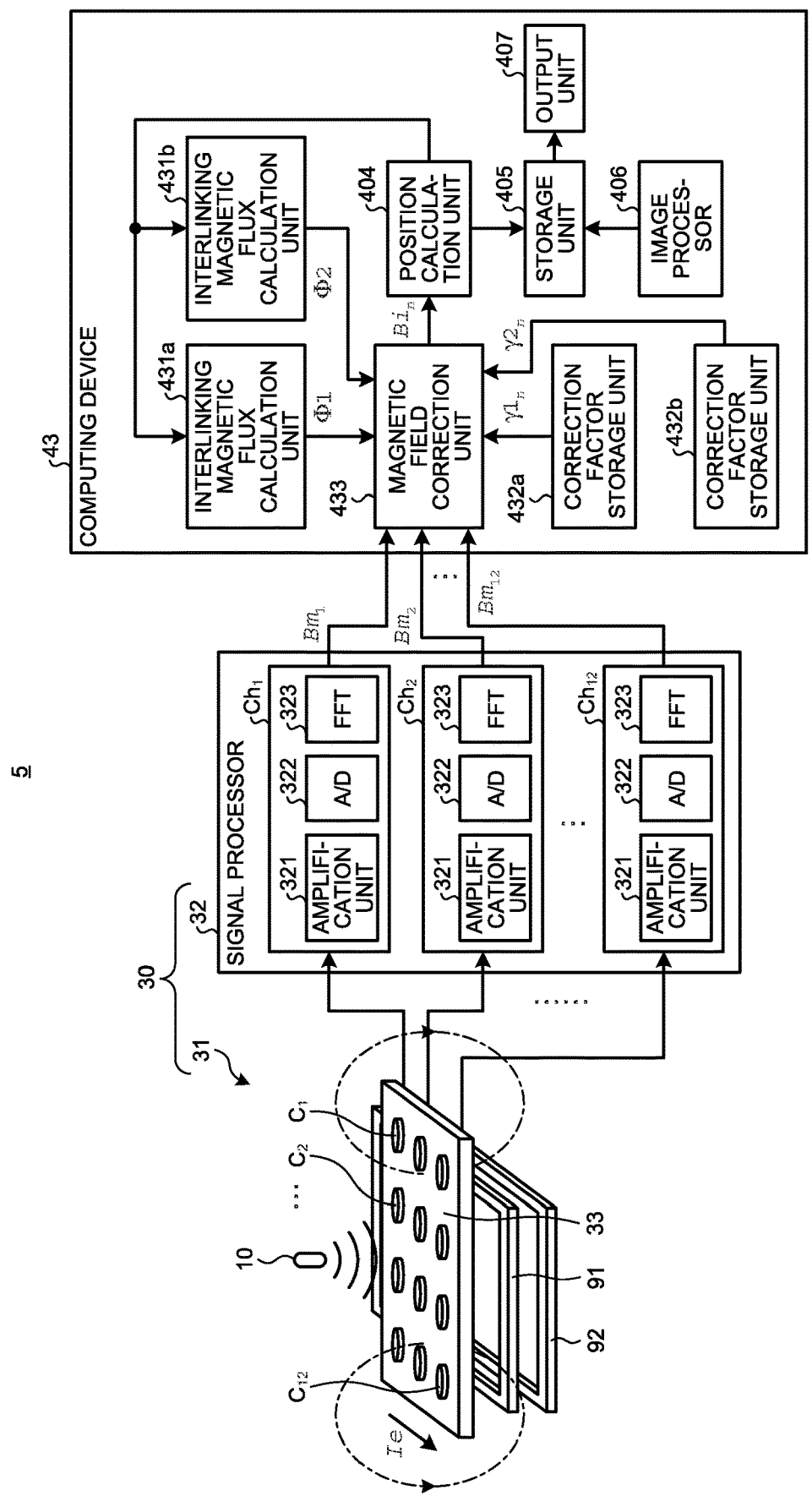
FIG. 11 is a diagram illustrating a configuration example of a position detection system according to a fifth embodiment of the disclosure.

Next, a fifth embodiment of the disclosure will be described. FIG. 11 is a diagram illustrating a configuration example of a position detection system according to the fifth embodiment of the disclosure. As illustrated in FIG. 11, a position detection system 5 according to the fifth embodiment is provided with the magnetic field detection device 30 which includes the coil unit 31 and the signal processor 32, a computing device 43, and a plurality of (two in FIG. 11) metal components 91 and 92 which serve as interference magnetic field generation sources. Among these, the configuration and the operation of the magnetic field detection device 30 are the same as those according to the first embodiment.

Figure 12:
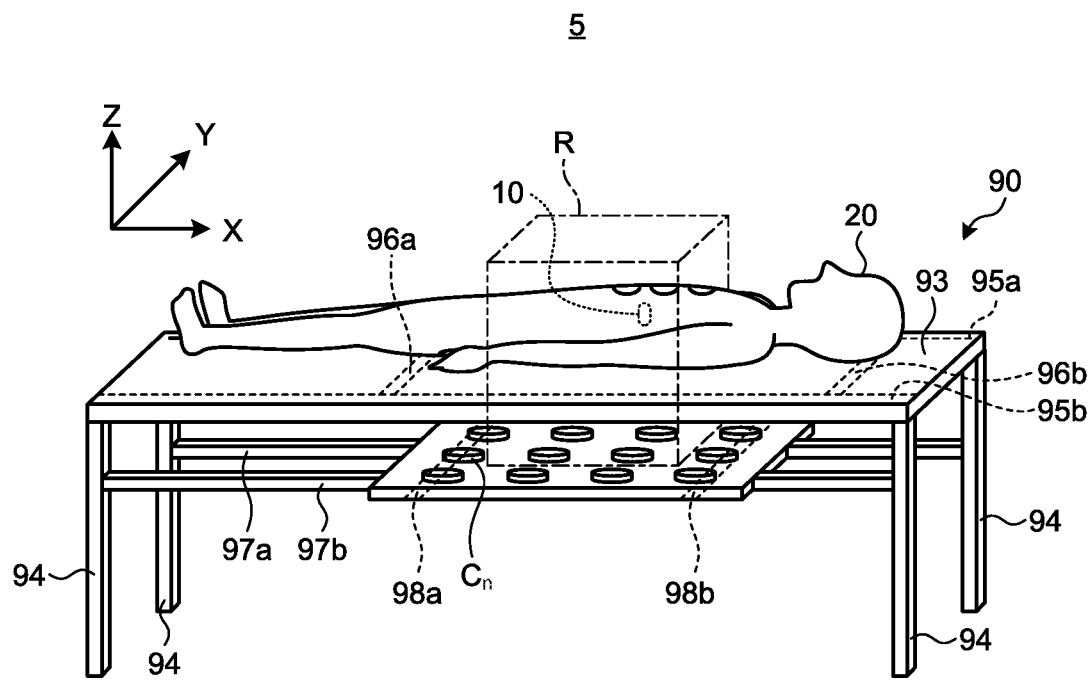
FIG. 12 is a schematic view illustrating a specific example of a metal component illustrated in FIG. 11.

FIG. 12 is a schematic view illustrating a specific example of the plurality of metal components 91 and 92 illustrated in FIG. 11, and illustrates a bed 90 on which the subject 20 is placed. This bed 90 is configured of a base portion 93 which allows the subject 20 to lie down thereon, four leg portions 94 which support the base portion 93, base support members 95*a* and 95*b* which are provided in the base portion 93 as a support frame of the bed 90, reinforcing members 96*a* and 96*b* which are bridged between these base support members 95*a* and 95*b*, support members 97*a* and 97*b* which are fixed to the leg portions 94, and coil holding members 98*a* and 98*b* which are bridged between these support members 97*a* and 97*b*. All the members are formed using metal.

Figure 13:
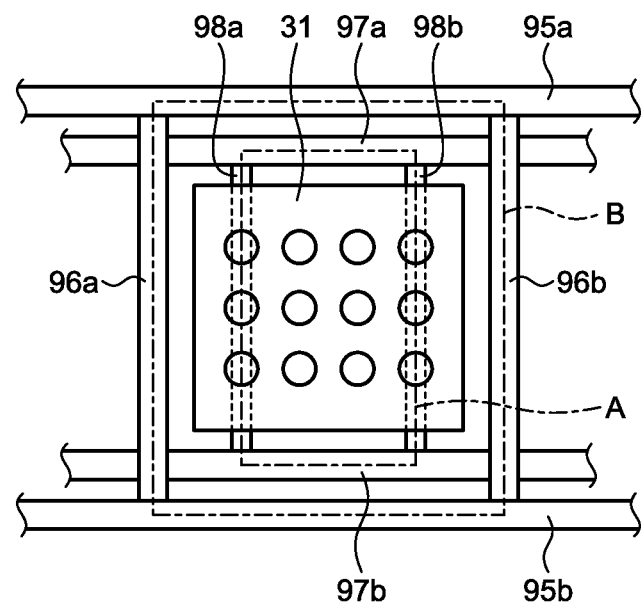
FIG. 13 is a top view illustrating a support frame illustrated in FIG. 12.

FIG. 13 is a top view illustrating a part of the support frame illustrated in FIG. 12. In the fifth embodiment, the support frame that supports the base portion 93 and the coil unit 31 is intentionally formed to have a loop shape. That is, a loop A is formed using each part of the support members 97*a* and 97*b* and the coil holding members 98*a* and 98*b*, and a loop B is formed using each part of the base support members 95*a* and 95*b* and the reinforcing members 96*a* and 96*b*. These loop A and loop B correspond to the metal components 91 and 92 illustrated in FIG. 11.

When the support frame including the loop A and the loop B is formed using metal in this manner, it is possible to secure the intensity required for the bed 90, and further, it is possible to handle the loop A and the loop B, which serve as interference magnetic field generation sources with respect to a position-detecting magnetic field generated by the capsule endoscope 10, as a loop coil. Accordingly, it is possible to calculate interference magnetic fields generated from the loop A and the loop B, and to accurately correct a measurement value of the position-detecting magnetic field detected by each of the detection coils C.

Referring to FIG. 11 again, the computing device 43 includes a plurality of (two in FIG. 11) interlinking magnetic flux calculation units 431*a* and 431*b*, a plurality of (two in FIG. 11) correction factor storage units 432*a* and 432*b*, a magnetic field correction unit 433, the position calculation unit 404, the storage unit 405, the image processor 406, and the output unit 407. Among these, the operations of the position calculation unit 404, the storage unit 405, the image processor 406, and the output unit 407 are the same as those in the first embodiment.

The interlinking magnetic flux calculation unit 431*a* calculates an interlinking magnetic flux $\Phi 1$ with respect to the metal component 91 which is caused due to the position-detecting magnetic field generated from the capsule endoscope 10. In addition, the interlinking magnetic flux calculation unit 431*b* calculates an interlinking magnetic flux $\Phi 2$ with respect to the metal component 92 which is caused due to the above-described position-detecting magnetic field. The interlinking magnetic fluxes $\Phi 1$ and $\Phi 2$ can be calculated using Formulas (13) to (15) based on calculation results of a position and a posture of the capsule endoscope 10 obtained in the immediately previous calculation performed by the position calculation unit 404, which is similar to the third embodiment.

The correction factor storage unit 432a stores a correction factor $\gamma 1_n$ for correction of an interference magnetic field component, generated from the metal component 91, in the measurement value $Bm_n$ of the position-detecting magnetic field detected by each of the detection coils $C_n$. In addition, the correction factor storage unit 432b stores a correction factor $\gamma 2_n$ for correction of an interference magnetic field component, generated from the metal component 92, in the measurement value $Bm_n$ of the position-detecting magnetic field detected by each of the detection coils $C_n$. These correction factors $\gamma 1_n$ and $\gamma 2_n$ are acquired in advance and stored in the correction factor storage units 432a and 432b, respectively.

The magnetic field correction unit 433 calculates the ideal value $Bi_n$ of the position-detecting magnetic field by correcting the measurement value $Bm_n$ of the position-detecting magnetic field detected by each of the detection coils $C_n$. Herein, an interference magnetic field component $Bc1_n$ at each position of the detection coils $C_n$ generated by the metal component 91 and an interference magnetic field component $Bc2_n$ at each position of the detection coils $C_n$ generated by the metal component 92 are given based on the following Formulas (16-1) and (16-2), respectively.

$$Bc1_n = \gamma 1_n \times \Phi 1 \quad (16\text{-}1)$$

$$Bc2_n = \gamma 2_n \times \Phi 2 \quad (16\text{-}2)$$

Accordingly, the ideal value $Bi_n$ of the position-detecting magnetic field at each position of the detection coils $C_n$ is given based on the following Formula (17).

$$Bi_n = Bm_n - \gamma 1_n \times \Phi 1 - \gamma 2_n \times \Phi 2 \quad (17)$$

Next, a method of acquiring the correction factors $\gamma 1_n$ and $\gamma 2_n$ will be described by exemplifying the support frame illustrated in FIG. 13. FIG. 14 is a schematic view for describing the method of acquiring the correction factor in a case where the support frame illustrated in FIG. 13 is configured as the interference magnetic field generation source.

First, the base portion 93 and the base support members 95a and 95b supporting the base portion 93, and the reinforcing members 96a and 96b are detached from the bed 90 as illustrated in (a) of FIG. 14. Accordingly, a state where the loop A formed of the support members 97a and 97b and the coil holding members 98a and 98b is left is formed. In this state, the capsule endoscope 10 is arranged at a specific position inside the position detection region R to generate the position-detecting magnetic field, and a measurement value $Bm1_n$ of the position-detecting magnetic field detected by each of the detection coils $C_n$ is acquired.

Next, the coil holding members 98a and 98b are replaced by coil holding members 99a and 99b each of which is made of non-metal, such as resin, as illustrated in (b) of FIG. 14. At this time, a loop made of metal is not formed in the support frame, and it is possible to ignore the influence of the interference magnetic field. In this state, the capsule endoscope 10 is arranged at the specific position inside the position detection region R to generate the position-detecting magnetic field, and the measurement value of the position-detecting magnetic field detected by each of the detection coils $C_n$ is acquired as the ideal value $Bi_n$.

Next, the base support members 95a and 95b, and the reinforcing members 96a and 96b are installed again without changing each state of the coil holding members 99a and 99b as illustrated in (c) of FIG. 14. Accordingly, the loop B is formed using each part of the base support members 95a and 95b and the reinforcing members 96a and 96b. In this state, the capsule endoscope 10 is arranged at the specific position inside the position detection region R to generate the position-detecting magnetic field, and a measurement value $Bm2_n$ of the position-detecting magnetic field detected by each of the detection coils $C_n$ is acquired.

Next, the correction factors $\gamma 1_n$ and $\gamma 2_n$, which are given based on the following Formulas (18-1) and (18-2), respectively, are calculated using these measurement value $Bm1_n$, $Bm2_n$ and the ideal value $Bi_n$ and are stored in the correction factor storage units 432a and 432b, respectively.

$$\gamma 1_n = \frac{Bm1_n - Bi_n}{\Phi 1} \quad (18\text{-}1)$$

$$\gamma 2_n = \frac{Bm2_n - Bi_n}{\Phi 2} \quad (18\text{-}2)$$

Each of the interlinking magnetic fluxes $\Phi 1$ and $\Phi 2$ in Formulas (18-1) and (18-2) can be obtained using Formulas (13) to (15) based on the position and the posture of the capsule endoscope 10 at each time, which is similar to the third embodiment. Alternatively, a total value of components parallel to the direction of the interference magnetic field among the measurement values from the respective detection coils $C_n$ may be handled as the interlinking magnetic fluxes $\Phi 1$ and $\Phi 2$, which is similar to the first embodiment.

Incidentally, the coil holding members 99a and 99b made of non-metal are replaced by the coil holding members 98a and 98b made of metal again after acquiring the correction factors.

According to the fifth embodiment of the disclosure, the correction factor is calculated, in advance, for each of the metal components even when the plurality of metal components serving as the interference magnetic field generation sources with respect to the position-detecting magnetic field are arranged. Thus, it is possible to accurately correct the measurement value of the position-detecting magnetic field detected by each of the detection coils $C_n$.

Incidentally, even when three or more metal components are arranged, it is possible to perform correction in the same manner as the above-described fifth embodiment by providing the interlinking magnetic flux calculation unit and the correction factor storage unit for each of the metal components in the computing device 43.

According to Some embodiments, it is possible to exclude influence of an interference magnetic field in a detection signal of a magnetic field and to suppress an accuracy deterioration in a position detection operation.

The above-described first to fifth embodiments of the disclosure and modified example thereof are only examples for implementation of the present invention, and the present invention is not limited thereto. In addition, the present invention allows various inventions to be formed by appropriately combining a plurality of components disclosed in the above-described first to fifth embodiments and the modified examples thereof. The present invention can be modified in various manners in accordance with specifications. Further, it is obvious that other various embodiments can be implemented within a scope of the present invention, from the above description.

What is claimed is:
1. A position detection system comprising:
  a capsule medical device configured to generate a position-detecting magnetic field and configured to be introduced into a subject;

a plurality of detection coils arranged outside the subject, each detection coil being configured to detect the position-detecting magnetic field to output detection signal; and a processor comprising hardware, wherein the processor is configured to correct a magnetic field component caused by a first magnetic field generation material with respect to each of measurement values of detection signals output from the detection coils, the first magnetic field generation material being arranged inside a space that the position-detecting magnetic field generated by the capsule medical device present inside a detection target region is reachable, the detection target region being a region in which a position of the capsule medical device is detectable, the first magnetic field generation material being configured to generate a magnetic field due to action of the position-detecting magnetic field, wherein the processor is configured to correct the magnetic field component using a first correction factor which is a function of a measurement value of the position-detecting magnetic field detected by the detection coil in a state where the first magnetic field generation material is arranged inside the space and the capsule medical device is arranged at a specific position inside the detection target region, and a measurement value of the position-detecting magnetic field detected by the detection coil in a state where the first magnetic field generation material is not arranged inside the space and the capsule medical device is arranged at the specific position.

2. The position detection system according to claim 1, further comprising a magnetic field detector configured to detect a magnetic field at a position at which the first magnetic field generation material is arranged, wherein the processor is configured to correct the measurement values of the detection signals using an output value of the magnetic field detected by the magnetic field detector.

3. The position detection system according to claim 2, wherein the magnetic field detector is a coil wound along an outer circumference of the first magnetic field generation material.

4. The position detection system according to claim 3, wherein the first magnetic field generation material is a metallic plate.

5. The position detection system according to claim 1, wherein the first magnetic field generation material is a metallic frame which has a loop shape and supports a base portion on which the subject is placed.

6. The position detection system according to claim 1, wherein the detection coils are arranged on a same substrate, and
the first magnetic field generation material is a metallic frame which has a loop shape and is provided around the substrate to support the substrate.

7. The position detection system according to claim 1, wherein the processor is further configured to calculate at least one of a position and a posture of the capsule medical device using the corrected measurement values of the detection signals.

8. The position detection system according to claim 1, wherein the first magnetic field generation material has a loop shape forming a closed circuit, and
the first correction factor is a function of a measurement value of a magnetic field detected by the detection coil in a state where the first magnetic field generation material is arranged inside the space and a magnetic field having a specific intensity is generated at a specific position inside the detection target region, and a measurement value of a magnetic field detected by the detection coil in a state where the first magnetic field generation material is not arranged inside the space and a magnetic field having the specific intensity is generated at the specific position.

9. The position detection system according to claim 8, wherein the first correction factor is calculated based on a measurement value of the position-detecting magnetic field detected by each of the detection coils in a state where the capsule medical device is arranged at the specific position and the capsule medical device is caused to generate the position-detecting magnetic field.

10. The position detection system according to claim 8, wherein the first correction factor is calculated, in a state where power is supplied to the one detection coil among the detection coils so that a magnetic field is generated from the one detection coil, based on a measurement value of the magnetic field detected by each of the detection coils other than the one detection coil.

11. The position detection system according to claim 8, wherein the processor is further configured to:
calculate at least one of a position and a posture of the capsule medical device using the corrected measurement values of the detection signals;
calculate an interlinking magnetic flux to the first magnetic field generation material based on a relationship between the calculated at least one of the position and the posture of the capsule medical device, and an opening surface of the first magnetic field generation material; and
correct the measurement values of the detection signals using the calculated interlinking magnetic flux and the first correction factor.

12. The position detection system according to claim 11, wherein the processor is further configured to:
calculate a second interlinking magnetic flux to a second magnetic field generation material based on a relationship between the calculated at least one of the position and the posture of the capsule medical device, and an opening surface of the second magnetic field generation material that is arranged inside the space, has a loop shape forming a closed circuit, and generates a magnetic field due to action of the position-detecting magnetic field; and
correct the measurement values of the detection signals using the interlinking magnetic flux, the first correction factor, the second interlinking magnetic flux, and a second correction factor for correction of a magnetic field component caused by the second magnetic field generation material.

13. The position detection system according to claim 8, further comprising a base on which the subject is placed, wherein the first magnetic field generation material is a support material configured to support the base.

14. The position detection system according to claim 8, wherein
   the detection coils are arranged on a main surface of a panel having a planar shape, and
   the first magnetic field generation material is a support material configured to support the panel.

15. A position detection method comprising:
   detecting a position-detecting magnetic field to output a detection signal using each of a plurality of detection coils arranged outside a subject, the position-detecting magnetic field being generated by a capsule medical device introduced into the subject; and
   correcting a magnetic field component caused by a magnetic field generation material with respect to each of measurement values of detection signals output from the detection coils, the magnetic field generation material being arranged inside a space that the position-detecting magnetic field generated by the capsule medical device present inside a detection target region is reachable, the detection target region being a region in which a position of the capsule medical device is detectable, the magnetic field generation material being configured to generate a magnetic field due to action of the position-detecting magnetic field,
   wherein the correcting includes correcting the magnetic field component using a correction factor which is a function of a measurement value of the position-detecting magnetic field detected by each detection coil in a state where the magnetic field generation material is arranged inside the space and the capsule medical device is arranged at a specific position inside the detection target region, and a measurement value of the position-detecting magnetic field detected by the detection coil in a state where the magnetic field generation material is not arranged inside the space and the capsule medical device is arranged at the specific position.

* * * * *